US010397523B1

(12) United States Patent
Mitchell et al.

(10) Patent No.: US 10,397,523 B1
(45) Date of Patent: Aug. 27, 2019

(54) SYSTEM AND METHOD FOR CONTROLLING AND SELECTING SOURCES IN A ROOM ON A NETWORK

(71) Applicant: Image Stream Medical, Inc., Littleton, MA (US)

(72) Inventors: Eddie E. Mitchell, Harvard, MA (US); Peter Renzi, Acton, MA (US)

(73) Assignee: Image Stream Medical, Inc., Littleton, MA (US)

( * ) Notice: Subject to any disclaimer, the term of this patent is extended or adjusted under 35 U.S.C. 154(b) by 76 days.

(21) Appl. No.: 15/491,240

(22) Filed: Apr. 19, 2017

Related U.S. Application Data

(63) Continuation of application No. 13/708,903, filed on Dec. 7, 2012, now Pat. No. 9,654,739.

(60) Provisional application No. 61/568,013, filed on Dec. 7, 2011.

(51) Int. Cl.
*H04N 7/18* (2006.01)

(52) U.S. Cl.
CPC .................................. *H04N 7/181* (2013.01)

(58) Field of Classification Search
None
See application file for complete search history.

(56) References Cited

U.S. PATENT DOCUMENTS

| | | | |
|---|---|---|---|
| 6,002,398 A | 12/1999 | Wilson | |
| 2002/0167590 A1* | 11/2002 | Naidoo | G08B 5/004 |
| | | | 348/155 |
| 2007/0050828 A1* | 3/2007 | Renzi | H04N 7/15 |
| | | | 725/93 |
| 2009/0213140 A1 | 8/2009 | Ito et al. | |
| 2010/0157016 A1 | 6/2010 | Sylvain | |
| 2010/0257190 A1 | 10/2010 | Farkash et al. | |
| 2010/0325546 A1* | 12/2010 | Leo | G06F 19/321 |
| | | | 715/719 |
| 2012/0166996 A1 | 6/2012 | Leddell et al. | |

FOREIGN PATENT DOCUMENTS

EP          1143334          3/2005

OTHER PUBLICATIONS

Diane Gilmour, "Perioperative Care", Chapter 2, R. Pudner (Ed.), Nursing the Surgical Patient, 2nd Edition, London: Elsevier Science, 2005, pp. 17-33.

* cited by examiner

*Primary Examiner* — Christopher Braniff
(74) *Attorney, Agent, or Firm* — Finch & Maloney PLLC

(57) ABSTRACT

A system and method for controlling and selecting sources in a room on a network. The system allows a remote viewer to create a virtual presence within the room by providing the available displays, corresponding to the sources, to the remote viewer. The system includes a standardizing technique for improving the communication and overall switching of data for streaming on a network. The system can include a recording server for performing dual recording of the video files in each of a local database and a remote database. A graphical user interface (GUI) display is provided to guide a local user through a medical procedure in the standardized system.

20 Claims, 24 Drawing Sheets

SYSTEM AND METHOD FOR CONTROLLING AND SELECTING SOURCES IN A ROOM ON A NETWORK

RELATED APPLICATIONS

This application claims the benefit under 35 U.S.C. § 120 as a continuation of U.S. application Ser. No. 13/708,903 filed Dec. 7, 2012, entitled "SYSTEM AND METHOD FOR CONTROLLING AND SELECTING SOURCES IN A ROOM ON A NETWORK", which claims the benefit under 35 U.S.C. § 119(e) to U.S. Provisional Application Ser. No. 61/568,013, filed Dec. 7, 2011, entitled "SYSTEM AND METHOD FOR CONTROLLING AND SELECTING SOURCES IN A ROOM ON A NETWORK", all of which are hereby incorporated herein by reference in their entireties for all purposes.

FIELD OF THE INVENTION

The present invention relates to systems and methods for controlling a plurality of video and other information sources in a room connected through a network.

BACKGROUND OF THE INVENTION

In a hospital environment, it is crucial for all rooms, and more particularly, the various sources and personnel within each room to communicate effectively. The sources within the room can include a control computer, an overview camera, a microscope, a PACS (picture archiving and communication system) computer, an in-light camera, a surgical navigation system, a C-Arm in the room, an ultrasound system, a physiological monitor, a laparoscope, an endoscope, and other devices and instruments available in a room for performing a medical procedure or operation.

Communication in a room of a hospital network, or other appropriate network, is often hindered by the multitude of formats used for each source available in the room. It is a challenge to effectively communicate between the various sources using current communication and network techniques. There is a lack of a system that allows a single user to manipulate all sources within a room using a standardized technique. Current systems require complex switching to account for different formats and connectivities (i.e. some devices employ DVI, others employ HDMI, and yet others employ S-Video, or some combination thereof, etc.).

Furthermore, in the communication context, there are several systems and methods available that allow remote users to gain access to the room. These systems disadvantageously provide access to the sources themselves directly to the remote viewer. Accordingly, a local in-room user experiences undesirable interruptions and potential loss of control of the procedure and the devices and sources that perform the functions of the procedure.

It is desirable to avoid these and other disadvantages by providing a system that standardizes sources within a room for effective and efficient communication and provides an in-room user with exclusive control of the sources and the capture and/or display thereof while improving usability and streaming operating room (OR) workflow.

SUMMARY OF THE INVENTION

A system and method standardizes and controls communication within a hospital network or other appropriate medical environment network. The system allows a remote viewer to create a virtual presence in a room connected to the network. A virtual presence system can include a plurality of displays within a room that respectively correspond to a plurality of sources. A processing arrangement on a controller is provided that selects a display, in response to a selection by the remote viewer, to provide only the display of the source to the remote viewer. The selection and viewing by the remote viewer occurs free of interference to the local user during a medical procedure. This allows the local user within the room to have exclusive control of the sources in the room, free of control by the remote viewer. Further, the remote viewer has a virtual presence in the room by viewing based on the displays of sources and content available to the local user in the room. Illustratively, a virtual presence can be established by a plurality of cameras in the room (such as an operating room) that are dedicated to creating and maintaining the virtual presence, such that the context of the room determines the content available.

Illustratively, the system also can include a recording server that records the data corresponding to the plurality of displays within the room in a local database. This server can be in the room or remote. The recording server can also record the displays that are selected by the remote viewer in a local or remote database, thereby creating dual recordings of the displays as viewed within the room. This further allows for verification that all videos and pertinent data have been accurately and appropriately recorded. Sources available for the displays include a room overview camera, a microscope, a PACS computer, an in-light camera, a surgical navigation system, a C-Arm, an ultrasound system, a physiological monitor, a laparoscope and an endoscope, among others readily apparent to those having ordinary skill. More than one of a given device type can be active at any given time.

Additionally, locally within the room and/or at a remote location, a continuous-loop recording system can be provided. In an illustrative embodiment, the system includes a database and application that stores data from cameras (the virtual presence cameras, for example, or other cameras or devices within the room) onto the database. The continuous-loop recording system stores the data for a predetermined amount of time (for example, 1 day or 12 hours), and the data is available if something goes wrong. If there are no problems with a particular procedure continues to record in a loop, recording over previously recorded data such that a lesser amount of memory is employed to record.

A graphical user interface (GUI) display can be provided in connection with the virtual presence system that has a plurality of screens for guiding a local user through a medical procedure. The GUI can be provided using context-aware techniques to streamline the overall experience for the local staff and indirectly improve the patient experience.

To standardize the sources within the room and facilitate the in-room control by the local user, a controller or control computer can be provided that is operatively connected to a video matrix switch. The plurality of sources is also connected to the video matrix switch to perform a plurality of functions associated with the sources and other content in the room using the control computer. The system can also include a plurality of adapters, one for each of the control computer and each of the plurality of sources, so as to render the control computer and sources in a standard format to improve connectivity for various sources, for further control and manipulation of the sources by the local user.

BRIEF DESCRIPTION OF THE DRAWINGS

The invention description below refers to the accompanying drawings, of which:

FIG. 9 a diagram of is an exemplary GUI display showing a briefing screen of the runtime application for the medical operation, according to the illustrative embodiment;

FIG. 11 a diagram of is an exemplary GUI display showing a roomlink function screen of the runtime application for the medical operation, according to the illustrative embodiment;

FIG. 18 a diagram of is an exemplary GUI display showing a service and support screen of the runtime application for the medical operation, according to the illustrative embodiment;

DETAILED DESCRIPTION

A system and method for controlling and selecting sources and other content in a room on a network allows a local user to control a plurality of sources in a room. The system further enables a remote viewer to experience a virtual presence in the room using a control computer by selecting from available displays corresponding to sources in the room. The room is a room in a medical environment, such as, but not limited to, an operating room (OR) in a hospital. The term "medical environment" as used herein, refers to a location in which a surgical, diagnostic, therapeutic, or other medical procedure is performed. The medical environment, or "medical treatment location" (used interchangeably herein) typically, but not always, has a doctor, hospital staff, and other medical personnel present, that assist in a medical procedure. The medical environment includes, but is not limited to, a hospital, trauma center, doctor's office, surgical center, and other locations known to those having ordinary skill in the art. The room can be a pathology room or a catheter lab, or other room in which a procedure occurs.

Figure 1:
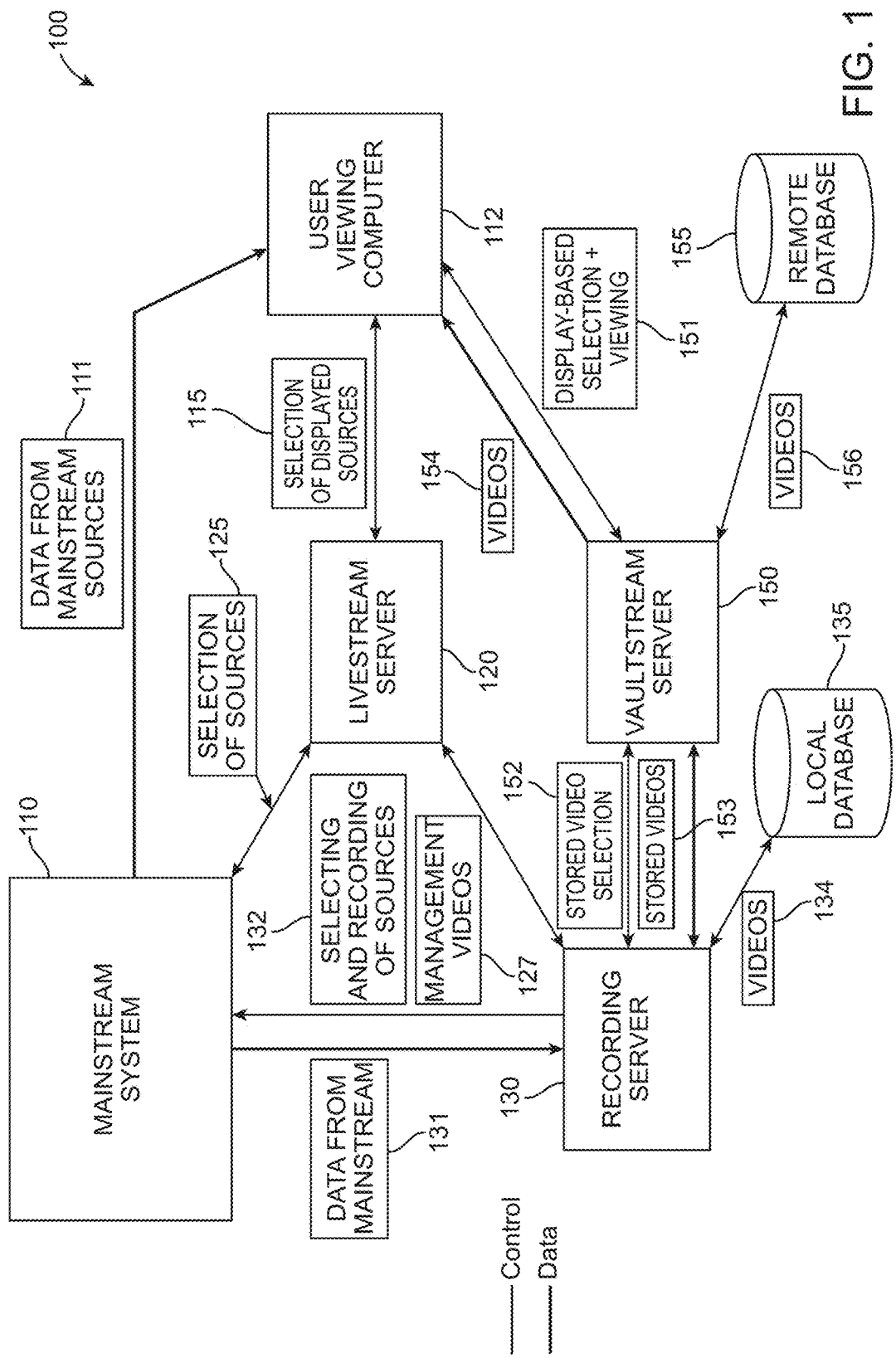
FIG. 1 is an overview block diagram showing the overall components of system for controlling communication in a medical environment, according to an illustrative embodiment.

FIG. 1 is an overview block diagram showing the overall components of a control system 100 for controlling communication in a medical environment and the relative interaction therebetween. The control system 100 includes a MainStream™ or EasySuite™ system 110, a LiveStream™ Server 120, a Recording Server 130, and a VaultStream™ Server 150. It is noted that proprietary terms are used herein to reference each component of the system. Such terms are provided in part to assist the reader in understanding the structure and format of the illustrative embodiment. These terms are trademarks of assignee, Image Stream Medical, Inc. Additionally, the terms "EasySuite" and "MainStream" are interchangeable as used herein and refer to the system for controlling sources and content in the room, and the flow of data relating thereto.

The MainStream system 110, as will be described in greater detail hereinbelow with reference to FIG. 1, controls the sources in the room and provides data from the sources, via datastream 111, to a user viewing computer 112 where the connections are brokered by the LiveStream server. The user viewing computer is a remote viewer who receives data from the sources in the room but does not have control over the sources in the room. Accordingly, a display-based system is created such that only the available displays of the sources are provided to the remote viewer 112. In this manner, the display-based recording overcomes disadvantages of the prior art in which the source is sent to a database or other appropriate entity for recording. By recording and viewing based upon the data associated with the display, the system ensures that the appropriate data is stored. By sending only a source for recording, the prior art systems result in potentially recording the wrong device or nothing at all. In accordance with the illustrative embodiment herein, the display determines the recording, and thus the correct information is recorded. This further prevents requiring a user to manually select a particular source to be recorded. Once a user selects a source for viewing in a particular display, that is recorded, and any switch in source will likewise still be recorded, as it is provided on a display within the room.

A user viewing computer 112 selects one (or a plurality) of displays that are available in a room via datastream 115, which is interpreted by the LiveStream server 120 to select the sources via datastream 125 in the MainStream system 110. The available content sources are then displayed to the user viewing computer 112 so as to create a virtual presence in the room for a remote viewer, as though they are within the MainStream system 110. A version of the LiveStream server 120 is shown and described in co-pending commonly assigned U.S. patent application Ser. No. 11/510,337, entitled STREAMING VIDEO NETWORK SYSTEM, by Peter Renzi, et al., the teachings of which are incorporated by reference as useful background information, and also described in pertinent part below.

Figure 1A:
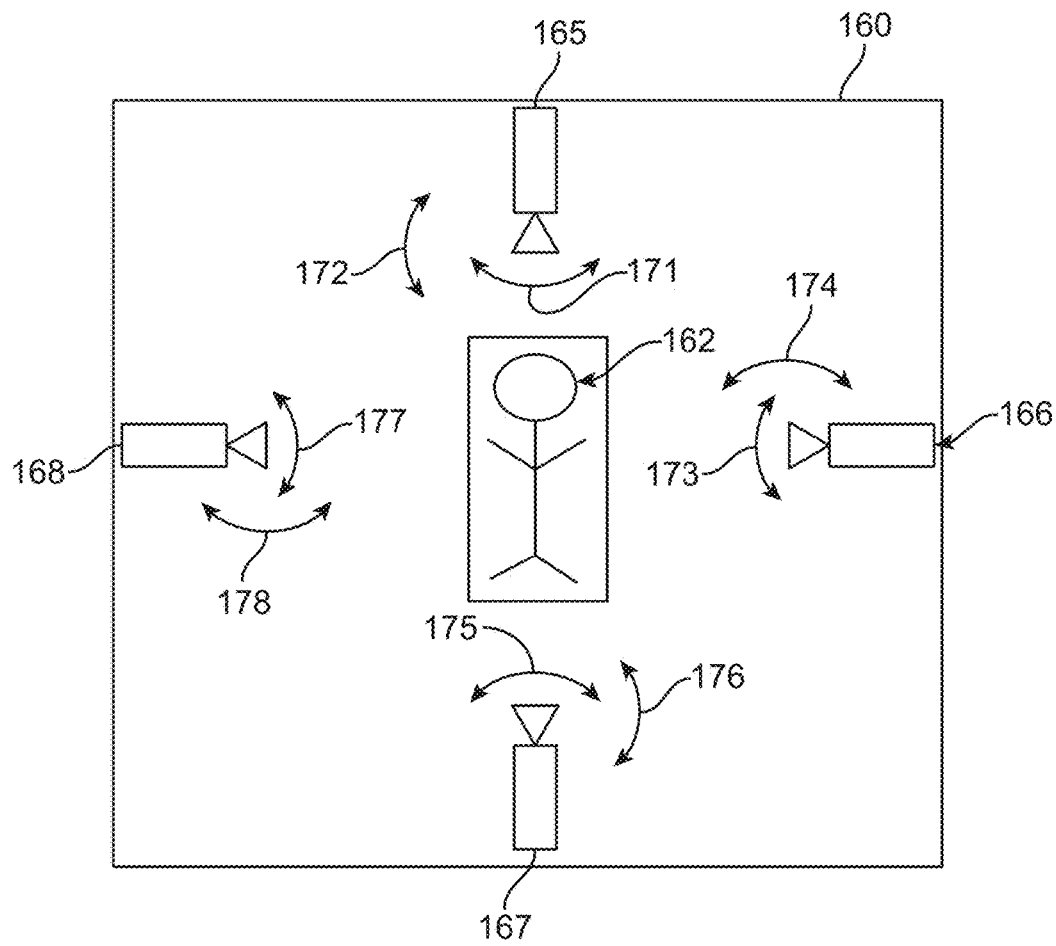
FIG. 1A is a schematic floor plan view of a patient in a room of a medical environment, including a plurality of cameras for creating a virtual presence in the room for a remote viewer, according to an illustrative embodiment.

Reference is now made to FIG. 1A showing a schematic floor plan view of a patient in a room of a medical environment (such as an operating room within a hospital). As shown, the room 160 has a patient 162 therein, and the room 160 includes a plurality of cameras 165, 166, 167 and 168 that are used to establish a virtual presence for a remote viewer as though they are in the room 160. Each of the cameras 165, 166, 167 and 168 can be standard pan/tilt/zoom (PTZ) cameras that move, respectively, in a panning back-and-forth direction 171, 173, 175, 177 and a tilting up-and-down direction 172, 174, 176 and 178. The cameras can also zoom inward and outward in accordance with ordinary skill. The virtual presence cameras 165, 166, 167 and 168 provide a full 360-degree view of the room 160 such that a remote viewer is able to view any angle and perspective of the patient during a medical procedure. More specifically, when a remote viewer establishes a connection to create the virtual presence, the viewer is first presented with a 360-degree view of the room to have a "lay of the land" perspective of the overall room. Once the user has the 360-degree view of the room, they are given a list of available displays, based upon the context of the room. As described in greater detail herein, the context of the room automatically determines the content that is available to the local user as well as the content available to remote viewers. Although four cameras are depicted in the room 160, any number of cameras from one camera to tens or hundreds of cameras can be employed to establish the virtual presence. In an illustrative embodiment, 4-6 cameras are in the room to provide sufficient data to establish a virtual presence, without providing too much information. The number of cameras is variable within ordinary skill depending upon the size of the room, the number of staff generally present within the room, and other factors readily apparent and applicable by those having ordinary skill in the art.

Referring again to FIG. 1, the MainStream system 110 also transmits data from the MainStream (in-room) active sources to a recording server 130 via datastream 131. The selecting and recording of active sources in the room is performed via datastream 132, and then data is transmitted via datastream 131 to the recording server 130. The control system 100 operates such that the selecting of active sources in the room is performed on the displays of the sources that are exclusively controlled by a local MainStream user within the MainStream system 110. Additionally, the virtual presence cameras (for example 165, 166, 167, 168 of FIG. 1A), allow a user to view the entire room from a 360-degree perspective as though they are in the center of the room, without having to enter into the medical environment. This can save critical time and space needed during a medical procedure, as well as reduce the risk of infection to the patient. Accordingly, a virtual presence is created for remote viewers as though the viewers are in the room that has the MainStream system 110 implemented therein. The system has the benefit of providing a presence for a remote user without requiring the person to be physically present in the room. This, for example, can save space without sacrificing the number of physicians available during a procedure. An expert at a remote location can be available for live assistance during a procedure, without having to be present at the location, and without having to be present in the room. The recording server 130, LiveStream server 120, and remote viewing computer 112 each are able to select available displays of the sources to be viewed, however the control of the sources themselves remains within the MainStream system 110 by a local user therein. It is expressly contemplated that the system supports a display based paradigm as well as virtual displays, which enable users to remotely select sources not assigned to physical displays in the room.

The displays and sources are collectively referred to as "content" herein. In an illustrative embodiment. The content of a room can automatically be determined by the context of the room. The context refers to the type of procedure, the status of the room, the state of the patient, equipment status, and determines a higher level of abstraction of a procedure to thereby determine the content (e.g., device) for a particular procedure. For example, if a patient is having laparoscopy performed, the context automatically determines that the content will include a laparoscope. Additionally, the content may change relative to the status of the room. For example, if a patient is entering into the room, the remote viewer will want to review the content of the virtual presence cameras, not the laparoscope. Accordingly, the content is determined by the context of the procedure (including patient context). As described in greater detail with reference to FIG. 22, the patient information can be automatically determined based upon standard HL7 (Health Level 7) messages transmitted within the medical environment network.

Live videos and/or recorded videos (on the recording server 130) are accessed via datastream 127 by the LiveStream server 120. The LiveStream server 120 is a broker that controls access to live content. This enables a remote viewer to access both live and recorded video files. The VaultStream server 150 receives requests from a user viewing computer 112 via datastream 151 to select and view data stored in the recording server 130. The VaultStream server selects stored videos and data via datastream 152 to be accessed by the recording server 130. The stored videos and data are transmitted to the VaultStream server 150 via datastream 153 and then provided to the remote user viewing computer 112 via datastream 154. In this manner, a user viewing computer can view both live and stored video and data based upon the sources available within the MainStream system, while enabling the control of the actual sources to be exclusively within the MainStream system. A user also has access to an optional second set of sources that can be remotely selected. The data from the MainStream system, including videos and other data, is transmitted from the recording server 130 via datastream 134 into a local database 135. This allows the videos to be stored in local database. Simultaneously, videos can be transmitted to a remote database 155 via datastream 156. Accordingly, a dual recording of the videos is stored in both a local database 135 and a remote database 155. This improves overall accuracy and efficiency of the system, and allows users to access both locally stored videos and remotely stored videos without waiting for lengthy file transfer operations. Further, verification can be performed to ensure that all videos are properly stored at both locations (see FIG. 21). The system is capable of supporting more than 2 channels in certain embodiments, as readily apparent within the scope of ordinary skill.

Figure 2:
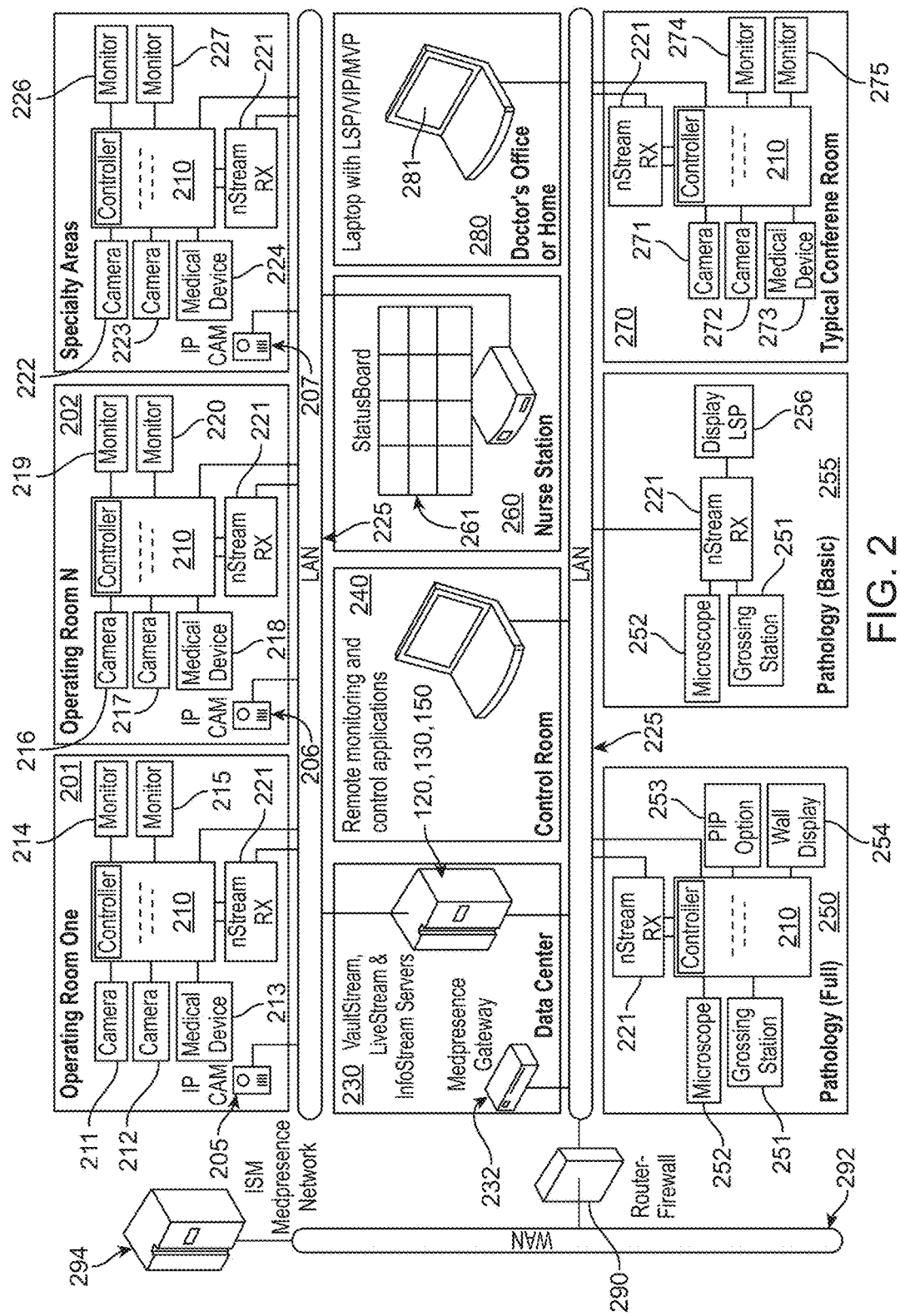
FIG. 2 is a network diagram showing the relative connectivity of the overall components of the system within the medical environment, according to the illustrative embodiment.
Figure 3:
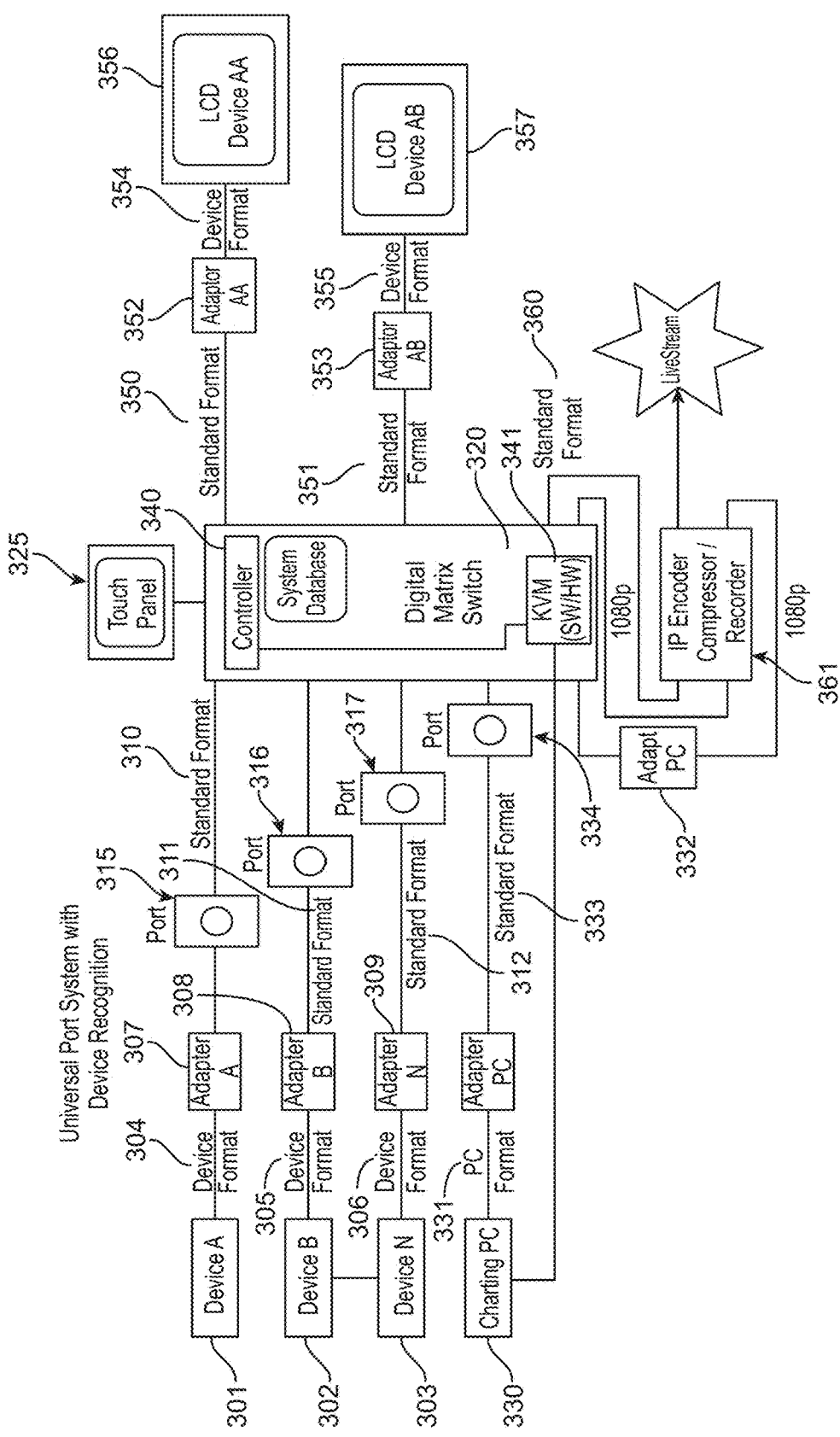
FIG. 3 is a schematic diagram of a room-based MainStream or EasySuite system, detailing an adapter configuration for standardizing communication between a plurality of devices and a video matrix switch to control system communication and video matrix switching, according to the illustrative embodiment.

Reference is now made to FIG. 2, a network diagram showing the relative connectivity of the overall components of the system within the medical environment. Each Operating Room 201 and 202 (Operating Room One 201, Operating Room N 202 and Specialty Area room 203) includes a MainStream system (110 of FIG. 1), the specific details of which are shown in FIG. 3, to standardize communication within the system. Each room includes a video router 210 having a plurality of sources 211-220, 222-224, 226, 227 (a camera 211, camera 212, medical device 213, monitor 214, monitor 215, camera 216, camera 217, medical device 218, monitor 219, monitor 220, camera 222, camera 223, medical device 224, monitor 226 and monitor 227). Refer to FIG. 3 for a more detailed view of the MainStream interconnectivity in accordance with the illustrative embodiments. In accordance with the illustrative embodiments, the plurality of sources are controlled exclusively by the local user during a medical procedure such that the remote viewer controls not the plurality of sources, but instead access to the sources via accessing the displays used during the medical procedures. The router 210 and an nStream RX device 221 are connected through a network 225, such as a Local Area Network (LAN) or other medical environment network, to a Data Center 230, which includes the VaultStream server 150, LiveStream server 120, and Recording server 130. Alternatively, all or part of the system can be interconnected using a wide area network (WAN). For example, one or more users can be in a site that is accessed by the well known Internet. Appropriate security, such as a Virtual Private Network (VPN) can be implemented to secure all or part of the Network in accordance with ordinary skill. Additionally, while not shown, the Internet can include appropriate security measures to comply with medical standards such as HIPAA (Health Insurance Portability and Accountability Act). HIPAA standards address the security and privacy of health data.

The Data Center 230 can also include a medpresence gateway computing platform 232 operatively connected to the servers 120, 130, 150. The medpresence gateway platform 232 has a virtual presence application running thereon that provides a virtual view to a remote viewer (for example on the medpresence network 294). The virtual view can be established on the medpresence network through video received from the virtual presence cameras (e.g. 205, 206, 207 or 165, 166, 167) located in room(s) of the medical environment. The virtual view can be a 360-degree view from combined camera views in accordance with ordinary skill. A "platform" as used herein refers to a hardware architecture and software framework that allows software, particularly application software, to run. Typical platforms include computer architecture, operating systems, programming languages, related user interface, and other platforms known in the art and readily applicable to those having ordinary skill.

The operating rooms 201, 202 and specialty area room 203 can also be connected through the network 225 to a control room 240 for remote monitoring and control applications. The control room 240 is employed in alternate embodiments for external control of the MainStream systems, as desired. Various other components and entities of the medical environment can also be connected through the network 225, including a full pathology room 250, a basic pathology room 255, a nurse station 260, a typical conference room 270 and a doctor's office 280.

The pathology room 250 is similar to any operating room in the control system, and includes a MainStream system for standardizing communication between sources within the room and overall communication. The pathology room 250 includes a router 210, operatively connected to a grossing station 251, a microscope 252, a PIP (picture-in-picture) option 253, and a wall display 254. A nStream RX device 221 is provided for appropriate connectivity to the network 225. The pathology room 250 is a full pathology room showing many available functionalities and hardware components available using the MainStream system. A basic pathology room 255 can also be employed, which includes a grossing station 251, a microscope 252, and a display (LSP) 256. An nStream RX device is capable of receiving two streams of input and converting into multiple streams. The RX device converges the recording and streaming so that the streams are sent to the server and the recording is sent to the server. The nStream RX device is capable of taking a single video input and turning it into three outbound streams of different resolution. For example, the RX device can take a single input stream and convert into a 480p, 720p and 1080p resolution output. The illustrative system employs a spatial matrix from a single stream to provide multiple output streams at varying resolutions. Multiple output streams at different resolutions is particularly useful in the medical context where the output stream can be predetermined based upon the particular source from which video is being streamed. For example, certain streams are desired to be in higher resolution, like certain streams can be in a lower resolution.

The nurse station 260 is also in communication through the network 225 and includes a status board 261 (shown and described in greater detail below with reference to FIG. 19) that provides displays of sources to the nurse station 260. A typical conference room 270 is connected through the network 225 and includes the appropriate MainStream system for standardizing communication that includes a video router 210. The conference room 270 includes a camera 271, a camera 272, a medical device 273 and monitors 274, 275, and is appropriately connected through nStream RX 221 for communication through the network 225. A doctor's office 280 includes a laptop 281 (or other appropriate device) connected through the network 225 for communication with entities on the network to create a virtual presence for a remote viewer in the doctor's office, as though the remote viewer were present in the room and able to view the displays as available to the local user.

The system can also be connected through an appropriate router-firewall 290 through a WAN 292 to a medpresence network 294 to establish a virtual presence for users in the room. The virtual presence is established through the gateway platform 232 operatively connected to system servers (e.g. 120, 130, 150). In accordance with illustrative embodiments, a client application on a computing device of a remote user or remote viewer of the medpresence network 294 is employed to select a display within the room of the medical environment, after the virtual view has been provided to the remote user on the medpresence network 294. Remote users can thereby establish the virtual presence in a room connected to the LAN 225, including the Operating Room One 201, Operating Room N 202, Specialty Area Room 203, full pathology room 250, basic pathology room 255 and typical conference room 270.

The MainStream system 110, shown by way of example, as Operating Room One 201, Operating Room N 202, full Pathology room 250, basic Pathology room 255 and Conference Room 270 in FIG. 2, provides control of in-room sources using a video matrix switch for standardizing the sources to improve communication. As shown in greater detail in FIG. 3, a plurality of devices, including Device A 301, Device B 302, and device N 303, are each operatively connected to a digital switch that switches between standard formats for communication within the system. Note that three devices are shown, but any number of devices may be provided up to 'N', representing any number of devices available within a room. The number of devices that can be connected to a single switch are limited by the inputs on the switch. However multiple switches may be employed within a room as appropriate to perform communication and streaming of information over the network. Advantageously, the system can be scaled as appropriate to include additional rooms, resources, etc., that can be implemented. Any appropriate wiring or package with switches, power indicators and the like can be implemented.

According to the standardized system, each device is provided with an adapter (adapter A 307 for device A 301, adapter B 308 for device B 302, and through to adapter N 309 for device N 303) which renders the device format 304, 305, 306 into a standard format 310, 311, 312 for the digital switch. This improves overall system connectivity by standardizing various formats for streaming via the switch. Moreover, ports 315, 316, 317 are provided for connectivity to the digital switch 320 so that the devices 301, 302, 303 can be quickly connected to the digital switch by simply connecting the appropriate adapter 307, 308, 309 into a port 315, 316, 317 of the digital switch 320. More particularly, in an exemplary embodiment, the devices includes formats such as SVideo (Separate Video), DVI (Digital Visual Interface), HDMI (High Definition Multimedia Interface), and other source formats. The adapters normalize the source-specific format into a standardized format for input to the switch. The standard output from the adapters can be DVI format and include a power channel and a data channel. Because the adapters are equipped with a power channel, no additional power is needed to perform the standardization of data. The switch 320 then switches only standardized formatted data and a single switch can accordingly be used for a plurality of differing type sources. An exemplary adapter configured to perform the standardization of format is performed implementing readily available video input chipsets, FPGA chips, FPGA firmware, and a chipset provided by Gennum Corporation of Burlington, Ontario, Canada for long distance video transport. The adapters provide appropriate connectivity for a source, depending on the output format type for the source. Adapters include the Gennum chipset to standardize the output from the source and include appropriate output connectivity to be connected to the switch for video streaming and other transmission. Adapters are also able to identify their corresponding source and relay this information to the switch using the data channel. Accordingly, there is no need to register the devices with the network or other systems, there is only a need to perform a one-time configuration with the adapter to its source, and the adapter can communicate the source identifying information through the switch.

A charting PC (personal computer) 330 is provided in the MainStream system to control the overall system and data pertaining to a patient. The PC format 331 is sent to the adapter 332, which provides a standard format 333 to the port 334. The port 334 is in communication with the switch 320 for further manipulation and control of the charting PC 330 output. The controller 340 is in communication with a software or hardware based keyboard, video and mouse switch (KVM) 341 and in communication with a system database 345. The controller 340 controls the KVM 341 to determine which computing device within the room will be controlled by the controller 340. In this manner, a single controller can perform the various functions of the system without requiring multiple keyboards, mice and displays for each computer. The computer 330 includes its own adapter for communication to the switch, and orchestrates the switching between the various computers and sources by switching keyboard and mouse using the KVM 341. Typical KVM switches also control video, however this embodiment controls only the keyboard and mouse for the various sources in the room. The KVM switch can be implemented in hardware or software in accordance with ordinary skill. Furthermore, the standard format improves communication and can be performed for other devices on the network when being sent from the digital switch 320.

The digital switch 320 transmits data in standard format 350, 351 to appropriate adapters that are connected to various devices within the room. Adapter AA 352 receives the standard format 350 and transmits appropriate device format 354 to device AA 356. Likewise, adapter AB receives the standard format 351 and transmits appropriate device format 355 to the device AB 357. In this manner, devices can appropriately receive data from the digital switch using a standard format by applying an adapter according to the system.

It is noted that the devices (A, B, . . . N, AA, AB) and various adapters (A, B, . . . N, AA, AB) are described hereinabove as being within a single "room", however any orientation is appropriate for a closed network in which the devices are used for performing a procedure. For example, the devices can represent various devices, cameras, monitors, and other sources that observe or are used during a surgery, operation, treatment or other medical procedure.

The digital switch 320 is also operatively connected to the LiveStream server through appropriate adapter and IP Encoder/Compressor 361 for outbound streaming of video files and other pertinent data. The standard format is transmitted from the switch via 360 to the Encoder/Compressor 361, which is then transmitted to LiveStream server 120. This can be performed, for example, using H264 encoding as appropriate for networked communication. Accordingly, the LiveStream server 120 can receive device data quickly and efficiently by applying adapters to the devices and employing a digital switch for switching the standardized data. Illustratively, the LiveStream server performs bi-directional communication with the room through the switch and appropriate encoders and decoders, as is readily apparent to those having ordinary skill. The LiveStream server essentially brokers the connectivity of all rooms through interconnectivity with a network.

Figure 4:
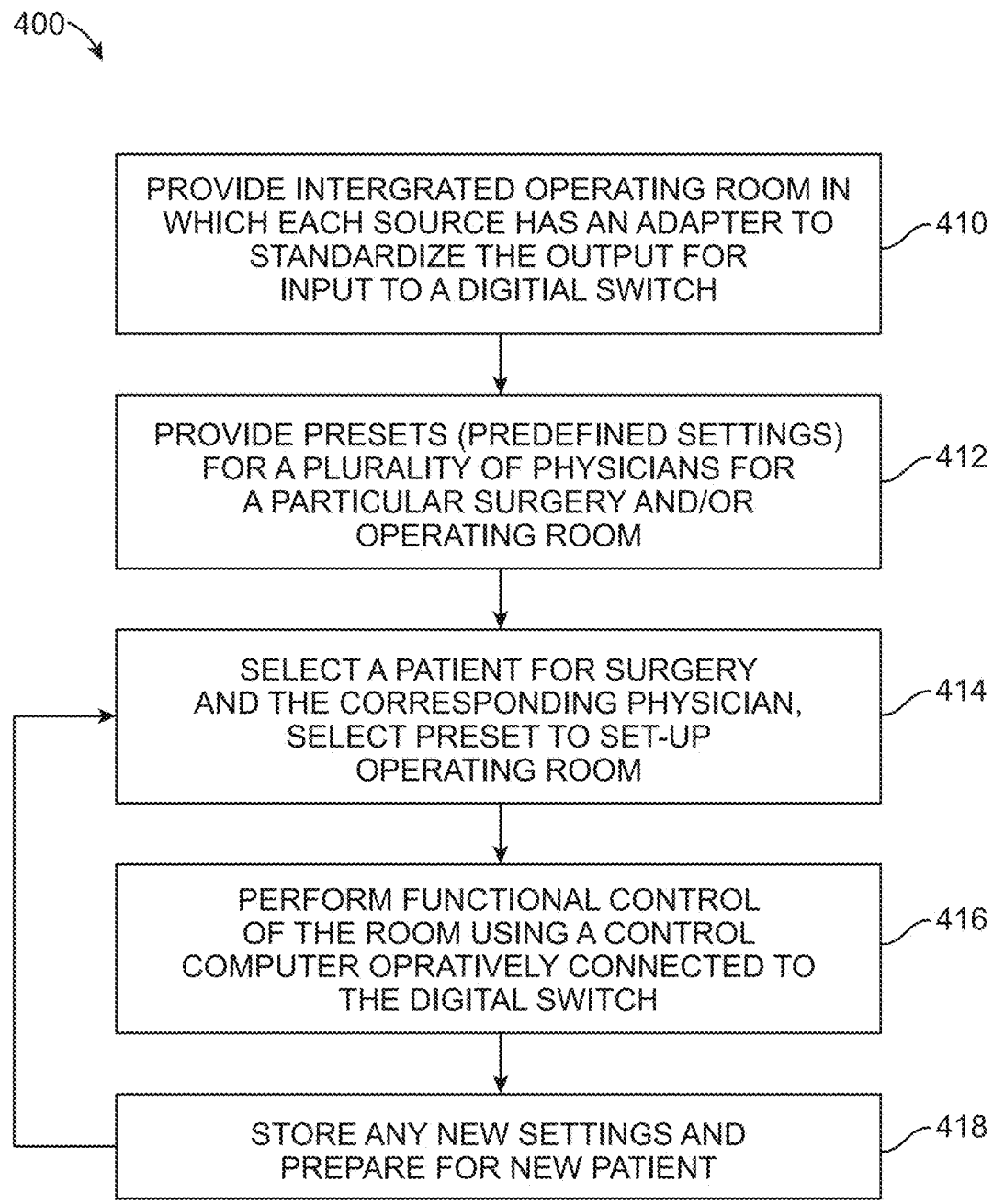
FIG. 4 is a flow chart showing a procedure for setting up a room, from an administrator's perspective, according to the illustrative embodiment.

Reference is now made to FIG. 4, showing a procedure 400 for integrating a MainStream system in a room, according to the illustrative embodiments. At step 410, the integrated operating room is provided in which each source has an adapter to standardize the output of the source for input to a digital switch. Each source within the room is provided with an adapter that standardizes the output of the device into a standard format, such as DVI. The adapter can also be used to appropriately format input to the device from a standard output of the switch. At procedure step 412, predefined settings are provided for a plurality of physicians for a particular surgery and/or operating room. In this manner, the particular settings that a physician prefers for each room and/or surgery being performed are readily available within the room. At procedure step 414, a local user selects a patient for surgery and the corresponding physician. The local user is then provided with the presets (predefined settings) for the room, and selects the preset to setup the operating room. The functional control of the room is performed at step 416, using a control computer operatively connected to the digital switch. The control computer can control all of the sources within the room through using the digital switch, as described herein. In an illustrative embodiment, the control computer is embedded into the EasyLink router and in further embodiments, the control computer can be external to the room. Any new settings are stored at step 418 and preparation for a new patient is performed. The process continues to repeat by returning to step 414 for each appropriate patient on which a surgery or operation is being performed. In this manner, the integrated operating room allows a plurality of patients to experience an improved medical operation.

Figure 5:
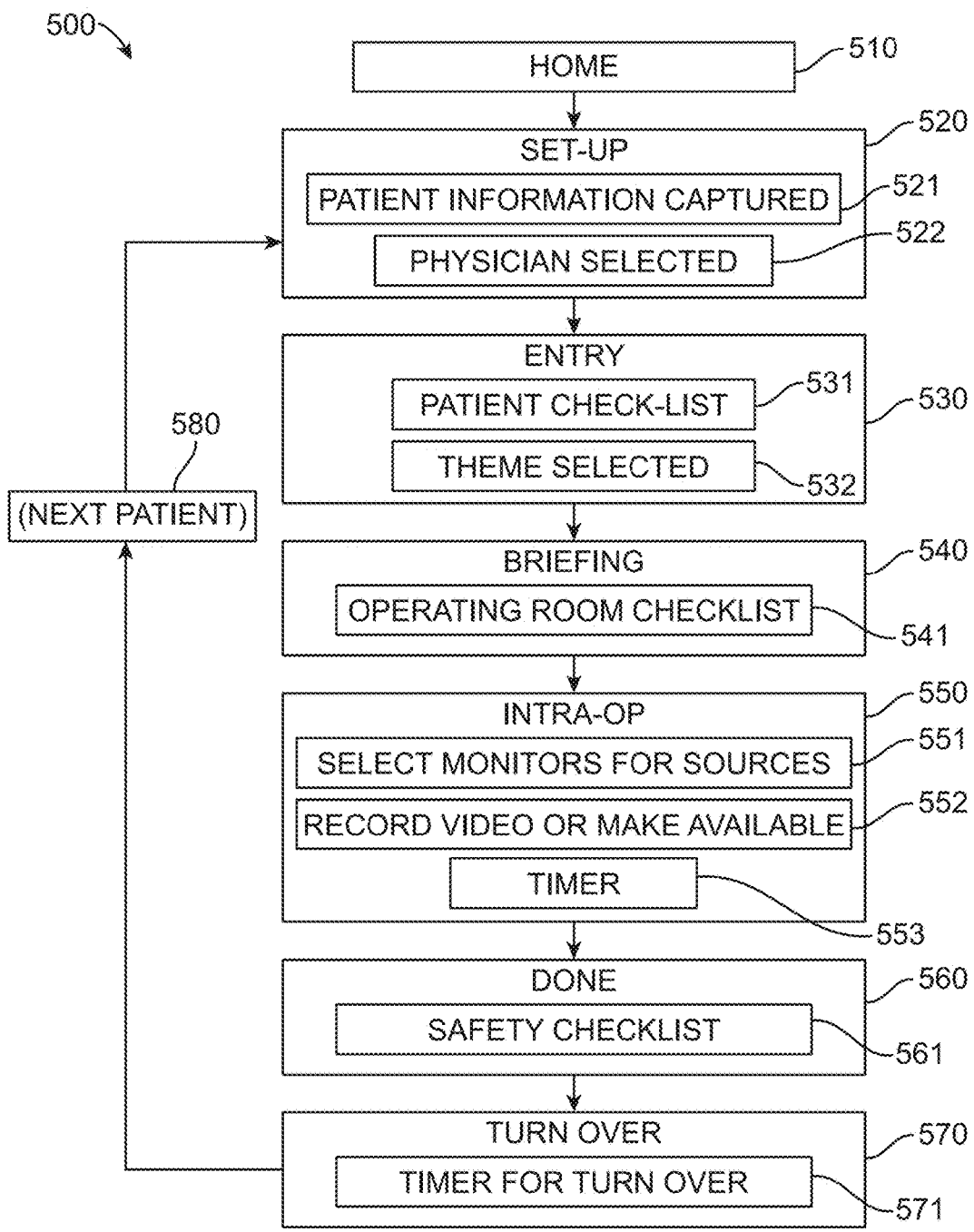
FIG. 5 is a flow chart of a procedure for a runtime application and the various stages present for performing a medical operation or other medical procedure, according to the illustrative embodiment.

FIG. 5 is a flow chart of a procedure 500 for a runtime application and the various stages present in an exemplary operation of the MainStream system, for performing a medical operation. The procedure 500 initializes with a home stage 510. See FIG. 6 for an exemplary screen display of a home stage of the procedure. The procedure then enters a setup phase 520, during which the patient information is captured 521, and the physician is selected 522. See FIG. 7 for an exemplary screen display of a setup stage of the procedure. The entry stage 530 includes a patient check-list 531 which verifies patient data, and a theme selected 532, in which a particular theme is selected for a patient. See FIG. 8 for an exemplary screen display of an entry stage of the procedure. This allows a local user to select a greeting system theme as appropriate for the patient. Alternatively, a patient can pre-select a desired theme to be emulated during the procedure. Notably, this improves the overall medical operation experience for a particular patient. For example, a patient interested in sports may select a sports theme, and various other patient-interest-oriented themes can be provided, as described herein. Another example is a child's cartoon character theme in a pediatric setting.

During the briefing phase 540, an operating room checklist 541 is verified to ensure operating room is prepared for the operation. See FIG. 9 for an exemplary screen display of a briefing stage of the procedure. An intra-op phase 550 occurs during the procedure, and allows the local user to select the monitors for the sources 551, and the local user selects which monitors will display the sources. See FIG. 10 for an exemplary screen display of an intra-op stage of the procedure. The particular displays that are selected or activated by the local user are the displays that are available to remote viewers. Remote viewers are only allowed to select and view the displays themselves, thereby ensuring that the local user who is physically in the room and performing or assisting in the medical operation has exclusive control of the functions of the procedure. Thereby a remote viewer cannot interfere with the procedure as the local user has exclusive control over the sources through a control computer. Advantageously, the remote viewer is provided with a virtual presence in the room which is illustratively restricted to viewing the particular displays available to a local user in the room. This particularly makes the user feel as if he or she is present and avoids "information overload" associated with other extraneous and/or unrelated sources and displays. During the intra-op 550 phase, a particular monitor can be made available 551 or a video can be recorded 552. Optionally, a timer 553 is also available in intra-op phase 550 for timing the procedure.

After the intra-op stage 550, the procedure enters a done phase 560, where a safety checklist 561 is provided and the user may complete the procedure by saving or discarding video, images and/or deciding whether or not to print images. See FIG. 12 for an exemplary screen display of a done stage of the procedure. Finally, during turn over stage 570, there is a timer provided for turn over 571. This allows the amount of time for a turn over to be tracked. A next patient 580 enters the room and the procedure returns to the setup stage 520 to gather patient information and resume the overall procedure from steps 520-570.

Figure 6:
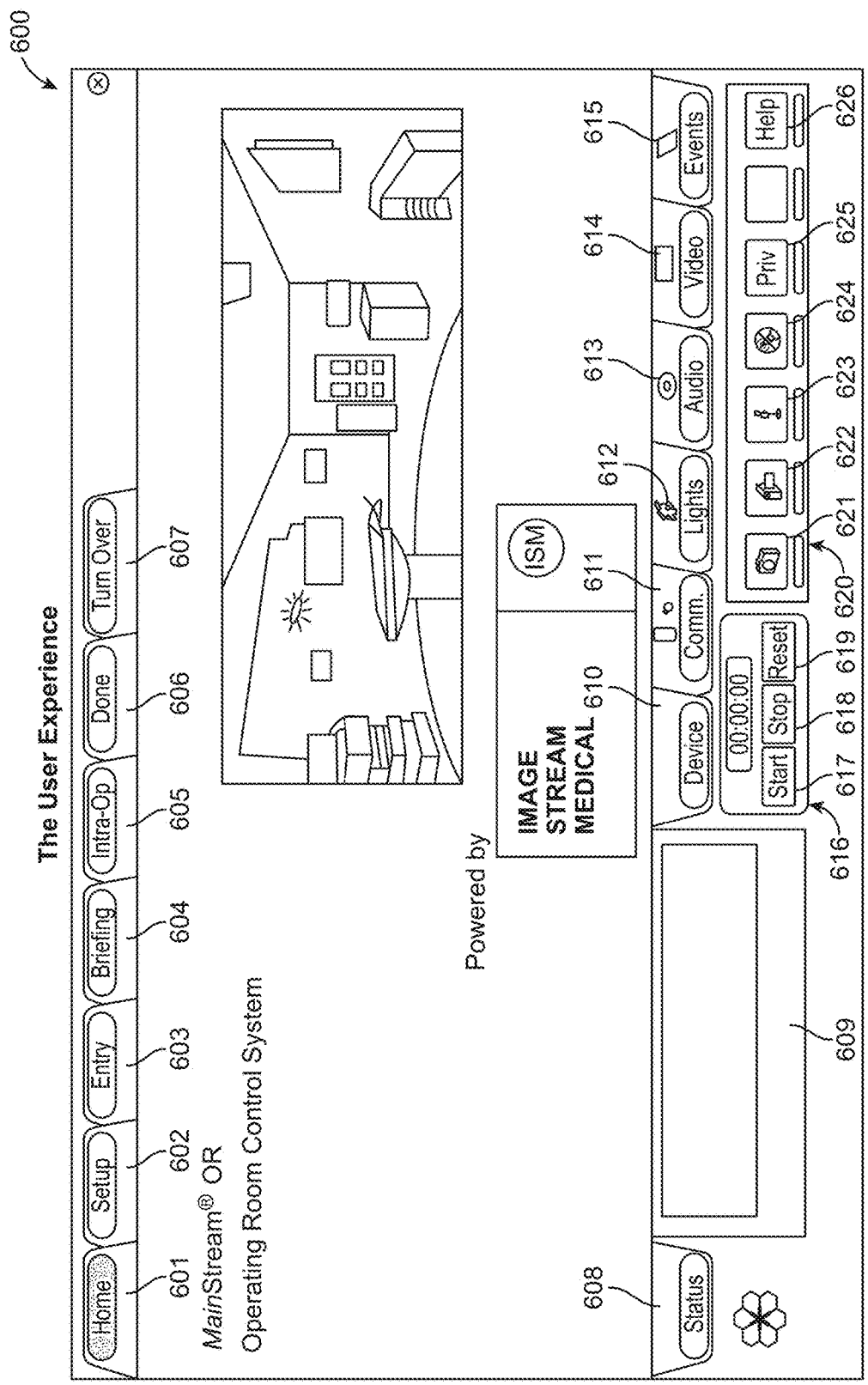
FIG. 6 is a diagram of an exemplary graphical user interface (GUI) display showing a home screen of the runtime application for the medical operation, according to the illustrative embodiment.

Reference is now made to FIGS. 6-17, showing diagrams of exemplary graphical user interface (GUI) displays for a plurality of screens, according to an exemplary runtime application for a medical operation or other surgical procedure. FIG. 6 shows a diagram of an exemplary GUI display of a home screen 600 of the runtime application. As shown, the screen 600 includes a plurality of workflow tabs for guiding a user through the runtime application of the medical operation. There is a home tab 601, a setup tab 602, an entry tab 603, a briefing tab 604, an intra-op tab 605, a done tab 606 and a turn over tab 607, each representative of the various stages of the runtime application for performing the medical operation. Each of the various stages will be shown in the following screen shots of FIGS. 7-13. Each screen includes each of the tabs for the various stages, as well as a status tab 608 to provide the status of the operation (see FIG. 18 for a status screen). Each page further includes function tabs with a device tab 610, Communication tab 611, Lights tab 612, Audio tab 613, Video tab 614, and Events tab 615, each of which will be described in greater detail hereinbelow. A timer 616 is provided on each page as a reference for local users and physicians performing the procedure, which includes a start button 617, a stop button 618 and a reset button 619. Each screen display also includes a global status bar 620 which provides a plurality of buttons for controlling the states of various systems connected to the controller. There is a camera button 621, video button 622, microphone button 623, internet signal button 624, privacy button 625 and help button 626.

Figure 7:
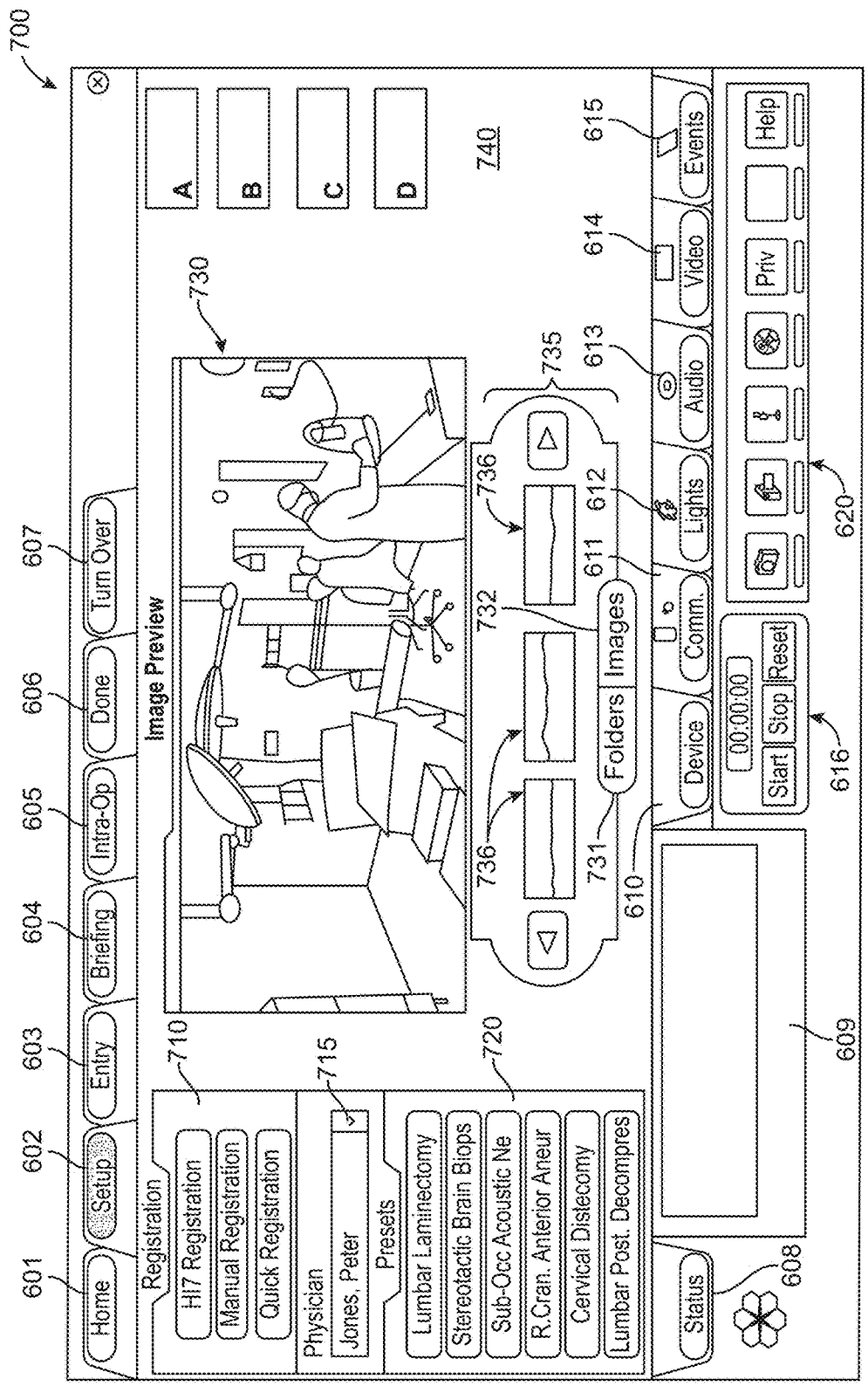
FIG. 7 is a diagram of an exemplary GUI display showing a setup screen of the runtime application for the medical operation, according to the illustrative embodiment.

From the home screen 600, a local user selects the Setup tab 602 and is directed to, for example, a setup screen 700 as shown in FIG. 7. The exemplary GUI display of FIG. 7 shows a diagram of a setup screen 70 including a registration panel 710 to perform registration of the patient and capture pertinent information; a physician selector 715, which provides a drop-down list to select the physician performing the operation. As shown, the registration panel 710 provides the user with the options to perform HL7 registration, manual registration or quick registration. A plurality of presets 720 is provided to allow the local user to select the settings for a particular operation. As shown, an image 730 is provided which displays the desired setup for the room, based upon the particular preset 720 that is selected. A local user selects the Folders icon 731 or the Images icon 732 to select the room setup photos to view for a particular preset. The image box 735 displays a plurality of thumbnail images 736 which can be selected to view a larger size image within the screen 730. The images 736 show the desired setup for a particular preset. Each of the monitors 740 are also displayed on screen 700 to show the desired display for each setup image. In further embodiments, the presets for a particular physician can be determined automatically based upon the HL7 registration, as shown and described in greater detail with reference to FIG. 8A.

Figure 8:
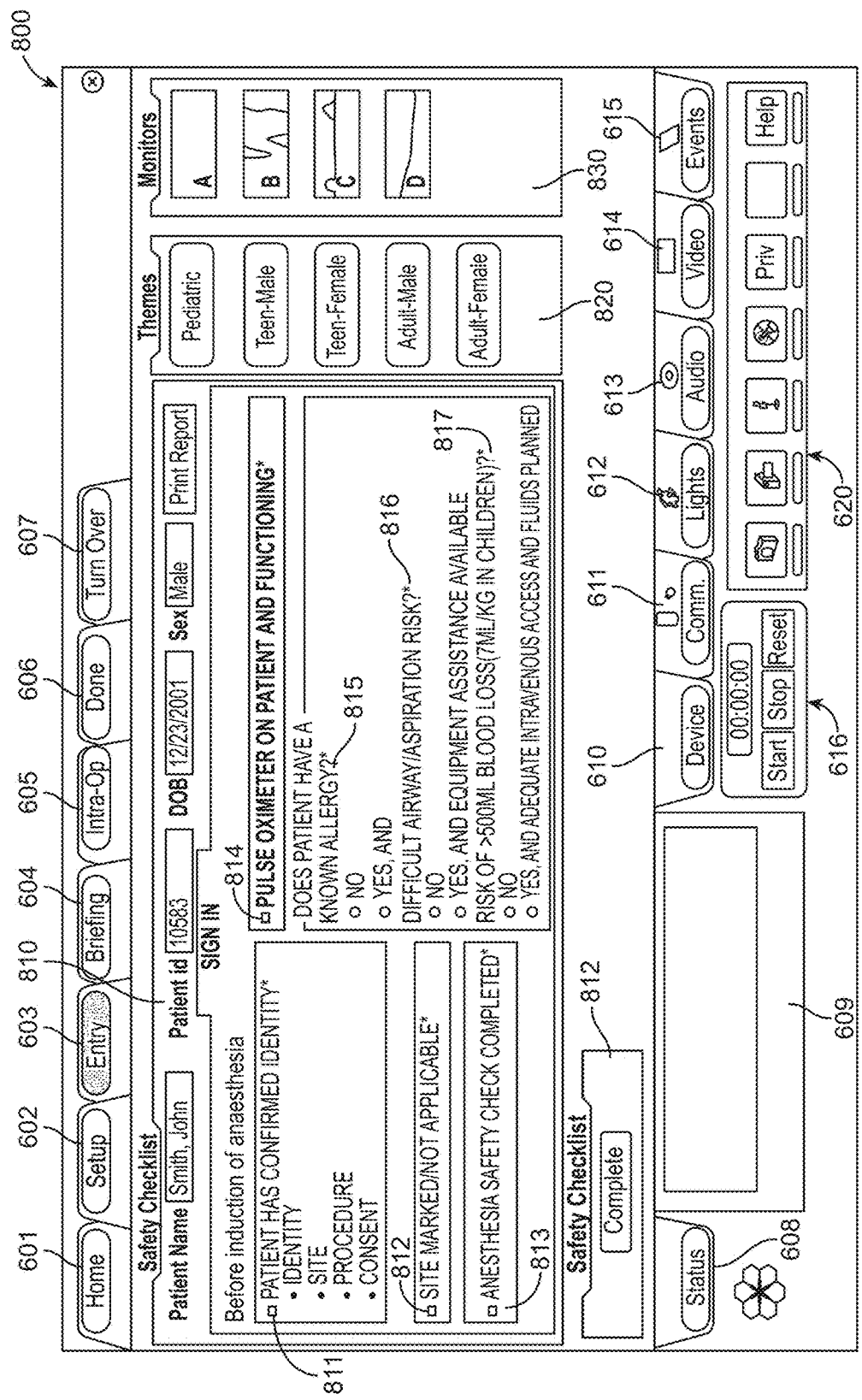
FIG. 8 a diagram of is an exemplary GUI display showing an entry screen of the runtime application for the medical operation, according to the illustrative embodiment.

FIG. 8 is a diagram of an exemplary GUI display showing an entry phase screen 800 which is presented to the local user upon selecting the entry tab 603. A safety checklist 810 is presented to the local user which provides a series of steps that the local user must perform prior to, for example in this screen, the induction of anesthesia. The local user first checks 811 whether the patient has confirmed identity, then checks point 812 whether the site is marked, then whether anesthesia safety check is completed at point 813 and finally point 814 whether the pulse oximeter is on the patient and functioning. Finally the local user checks whether the patient has a point 815 known allergy, point 816 airway/aspiration risk, and point 817 risk of blood loss. The checklist details are provided by the hospital and presented to the user by the system. The entry phase screen also provides the various themes 820 which allows the local user to select the theme as appropriate. As shown, themes can be specified based upon the patient, such as a Pediatric theme, a Teen-Male theme, a Teen-Female theme, an Adult-Male theme and an Adult-Female theme. The monitors 830 are also selected to show which images will be displayed on the various monitors for the various themes as a patient enters the room. Once the safety checklist is complete, the local user selects the complete button 812 to complete the entry phase.

Figure 8A:
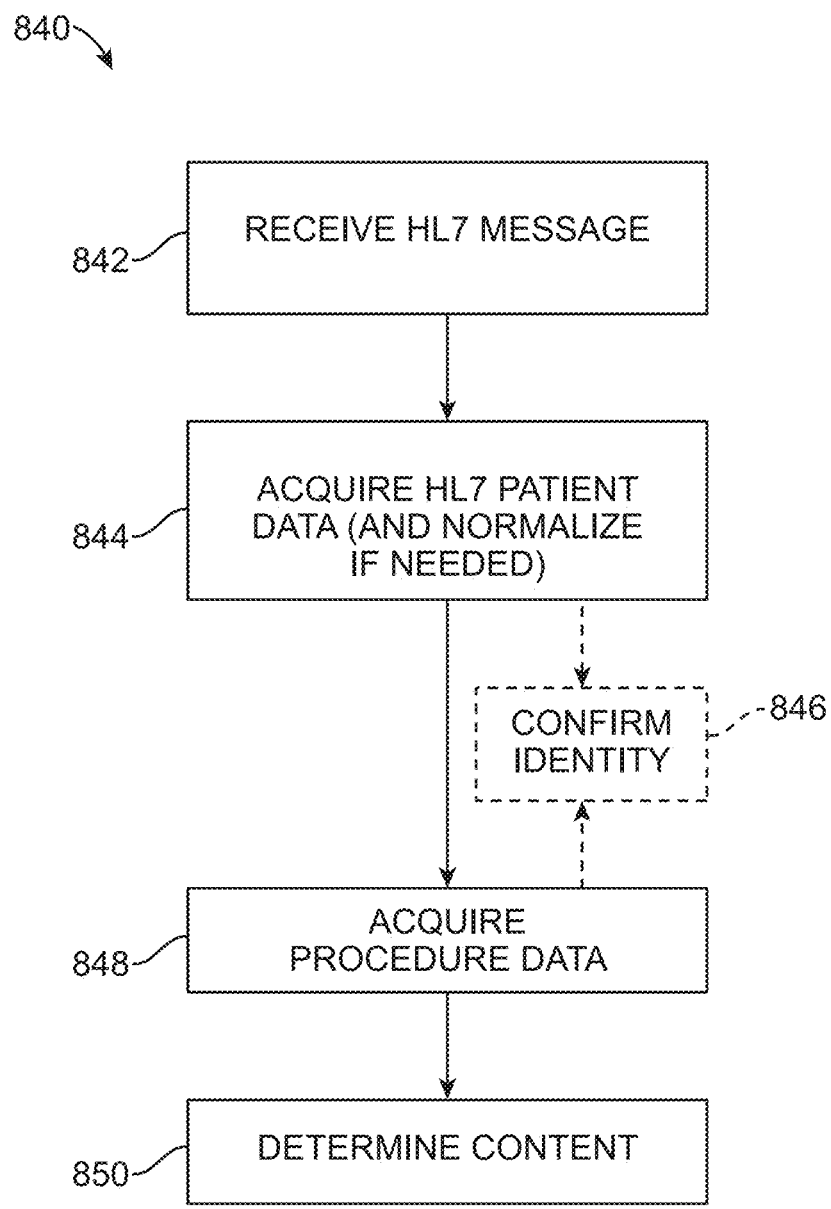
FIG. 8A is a flow chart of a procedure for automatically determining the context, and thereby the content, or a particular procedure, in accordance with the illustrative embodiments.

In accordance with the illustrative embodiments, the entry phase screen 800 can contain information that is obtained automatically based upon the HL7 messages for automatic registration, and corresponding procedure information available within the system or acquired automatically based upon the context (e.g. type of surgery, state of patient, equipment status, staff present) of the room. Accordingly, the checklist 810 of FIG. 8 is replaced with a list of patient information that is automatically determined from the system. The HL7 registration refers to acquiring patient information automatically in response to an HL7 message that is generated when a patient is admitted into a hospital. With reference to FIG. 8A, the procedure 840 for automatically determining room context, and corresponding content available in a room, commences at step 842 by receiving an HL7 message. An HL7 message is a message containing information that is standardized by HL7 (Health Level 7) and provides a framework for electronic health records. The system receives the HL7 message and then acquires the patient data from the message at step 844. The system further includes normalization techniques such that all data fields from HL7 messages can be appropriately correlated to the data field required by a particular hospital environment, such that the data can be normalized. For example, a system using "L.Name: Smith" and a system using "Last.Name: Smith" could be normalized so that they both have the particular required data field for recognition by the MainStream system, to be "LN: Smith". In certain embodiments, the identity of the patient can be confirmed at step 846. This can likewise be performed in an automated manner, such as a bar code scan of the bracelet on a patient, or by performing speech recognition or facial recognition on the patient. As an example, a patient could record a short voice message of their name upon admittance to the hospital. This could then be stored and sent with the HL7 message to later confirm identity of the patient. The patient could then speak their name and this could be compared to a stored voice message for the patient to confirm their identity. Facial recognition could also be employed to confirm identity of the patient as they enter the room.

Once the patient data has been acquired, procedure data is then acquired at step 848, either by manual entry by the user or through automated data transfer of the particular procedure that is related to the patient associated with the HL7 message. The procedure data can also be acquired by determining the status of the procedure based upon the location of persons within the room and status of equipment in the room. At step 850, the content (e.g. sources and displays) associated with the patient and procedure are determined. The contextual factors (i.e. patient status and procedure status) can automatically determine the content of the room. For example, if no equipment is in use and the patient is entering the room, the status can be assigned "entry" and the associated presets for types of content can be set, as defined by a physician or in accordance with hospital or HIPAA standards for care during a procedure. If the context determines that a laparoscopy is to be performed, then the content includes a laparoscope and is set to a desired display, as determined by a physician, or in accordance with HIPAA standards. In this manner, when a patient enters into a room, the room becomes context-aware that the patient has entered the room, based upon the HL7 messages. This advantageously reduces the chances of a problem during surgery by properly identifying the patient and the particular procedure to be performed. In addition, a burden is removed from the circulating nurse responsible for managing the operating room during the procedure, as he/she no longer needs to manually enter data into redundant systems.

Figure 9:
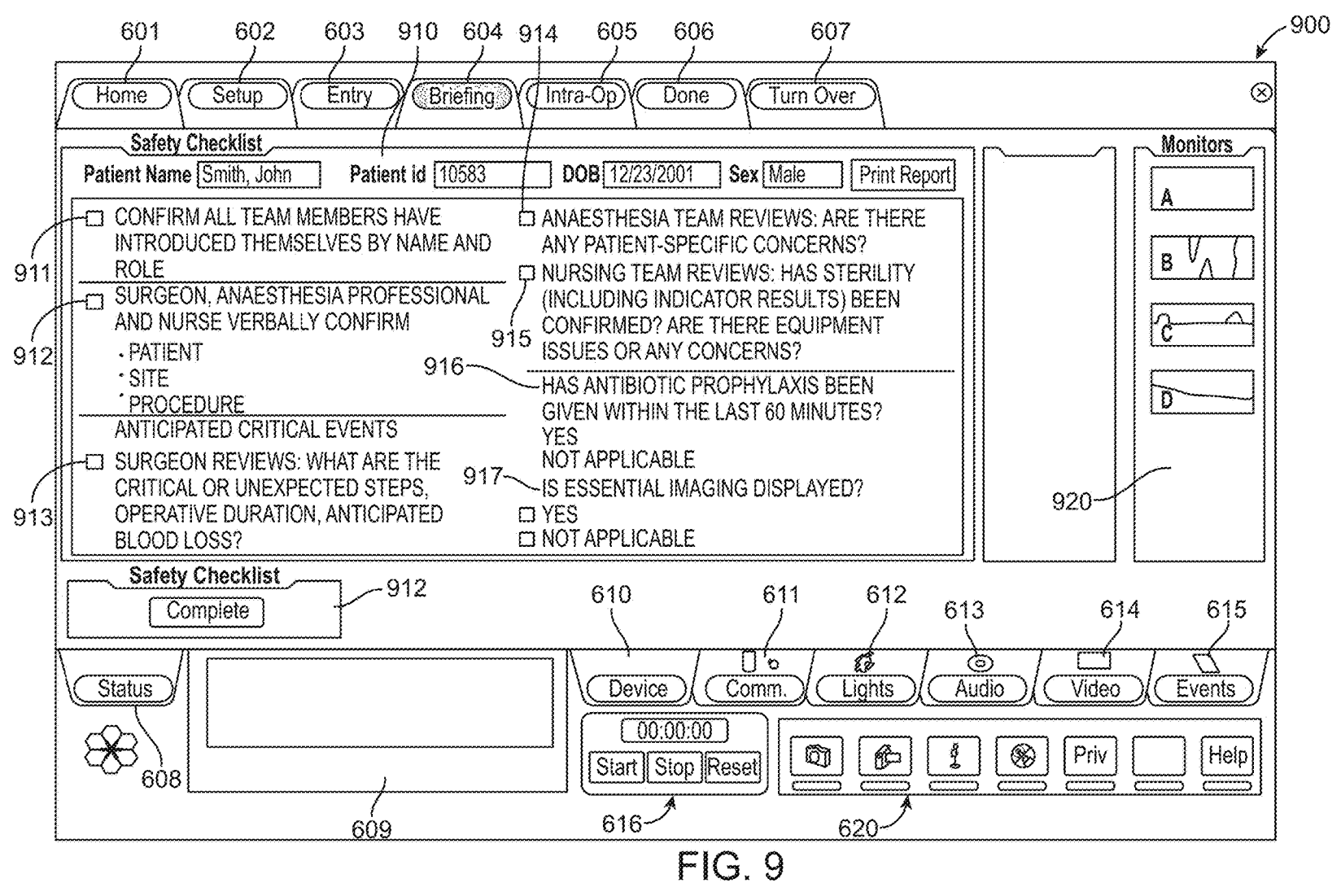

Next, during the briefing phase, a local user is directed to the exemplary GUI display of FIG. 9 showing a diagram of a briefing phase screen 900. A safety checklist 910 is presented to the local user to be performed prior to proceeding to the medical operation. The checklist includes point 911 to confirm all team members, point 912 to verbally confirm surgery details, then anticipated critical events point 913 surgeon reviews, point 914 anesthesia team reviews and point 915, nursing team reviews. Finally, safety checklist point 916 to check whether antibiotic prophylaxis has been given and point 917 whether essential imaging is displayed. The monitors are shown in the panel 920, and display the data available from the sources in the room. Once the safety checklist is complete, a local user can select the Complete button 912 to enter the next phase of the procedure. Again, the detailed items within the checklist are illustratively provided by the hospital.

Figure 10:
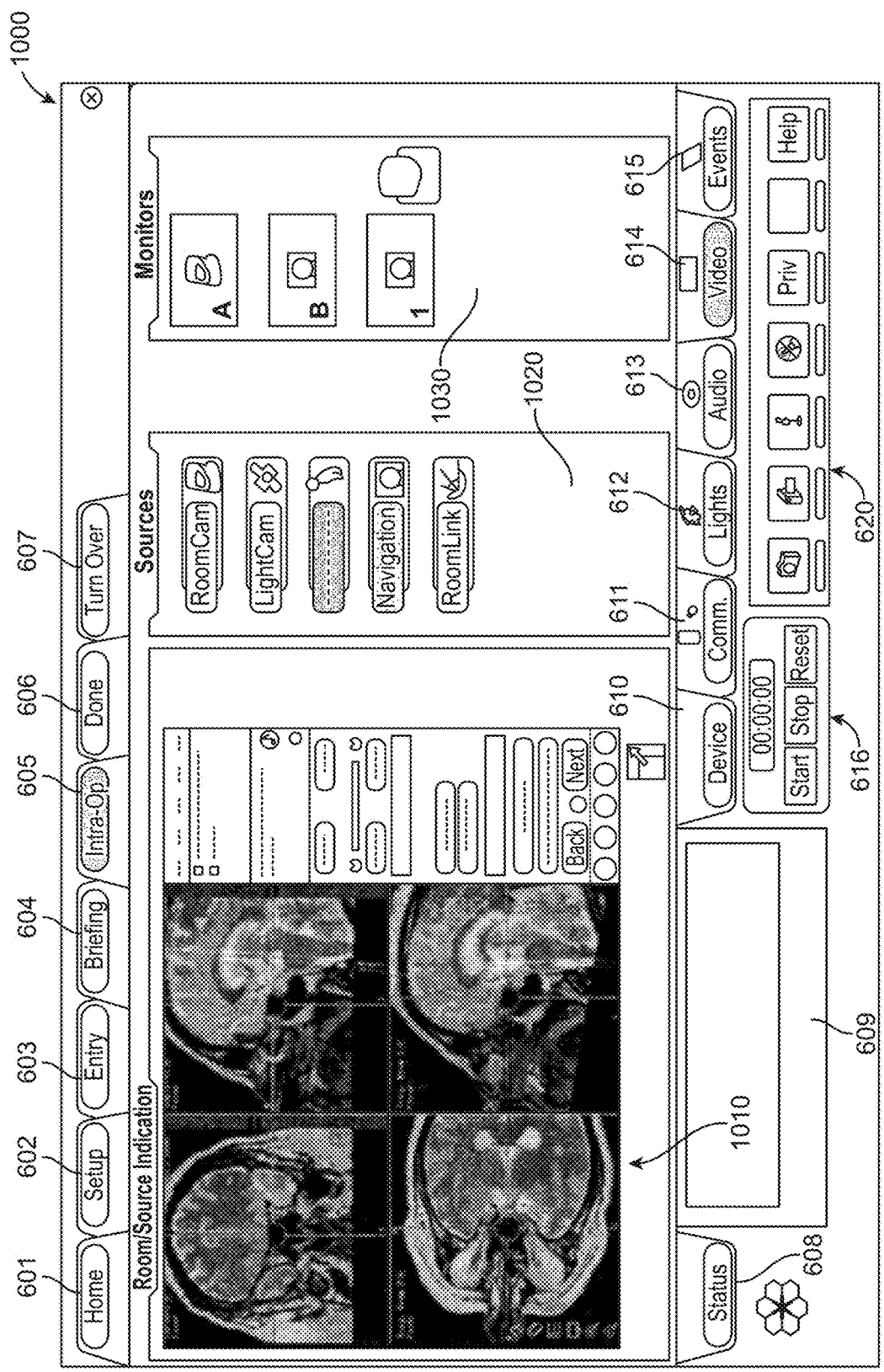
FIG. 10 a diagram of is an exemplary GUI display showing an intra-op screen of the runtime application for the medical operation, according to the illustrative embodiment.

During the intra-op phase of the medical procedure, a local user is directed to a intra-op screen 1000, for example as shown in the diagram of the exemplary GUI display of FIG. 10. A local user selects the monitors 1030 for the various sources 1020 during the intra-op stage, which become the "activated" or selected sources within the room. A source is shown in the display 1010. The activated sources, shown in monitors A, B and C in 1020, are the displays available to the remote viewer. From the intra-op screen, the user may choose the RoomLink function, which allows the user to create a connection to another room or location using the LiveStream system.

Figure 11:
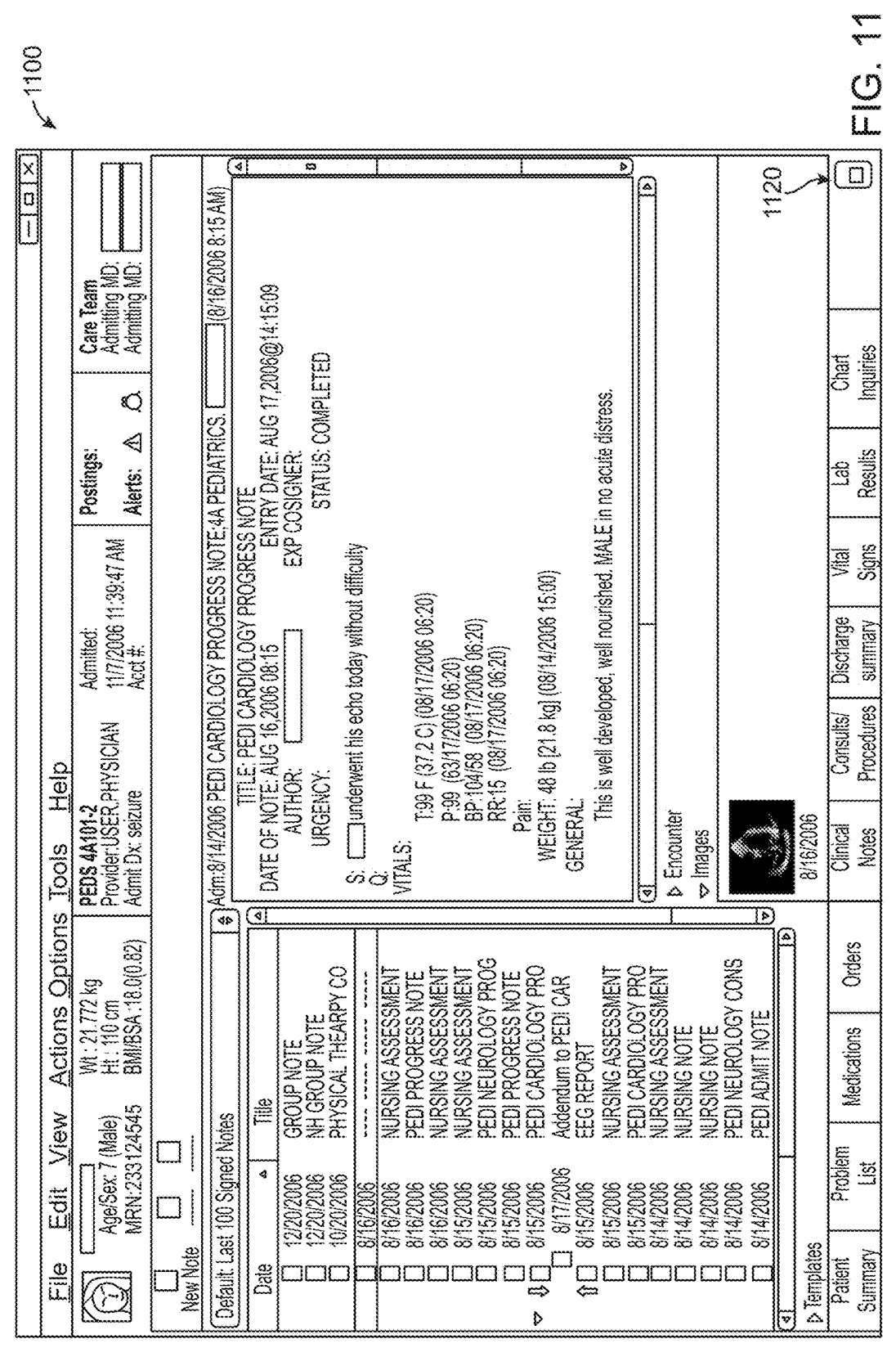

An exemplary GUI display showing a diagram of a nurses charting function screen 1100 is shown in FIG. 11. This shows the exemplary data presented about a patient upon a selection of the Events or EMR function tab. When in this mode, the user has full keyboard and mouse control of the nurse PC, and is able to enter data normally. This allows a user to sit at and operate through a single keyboard, mouse and display configuration while having control of multiple other computers and devices. To return to the main control interface is accomplished by selecting the close button 1120.

Figure 12:
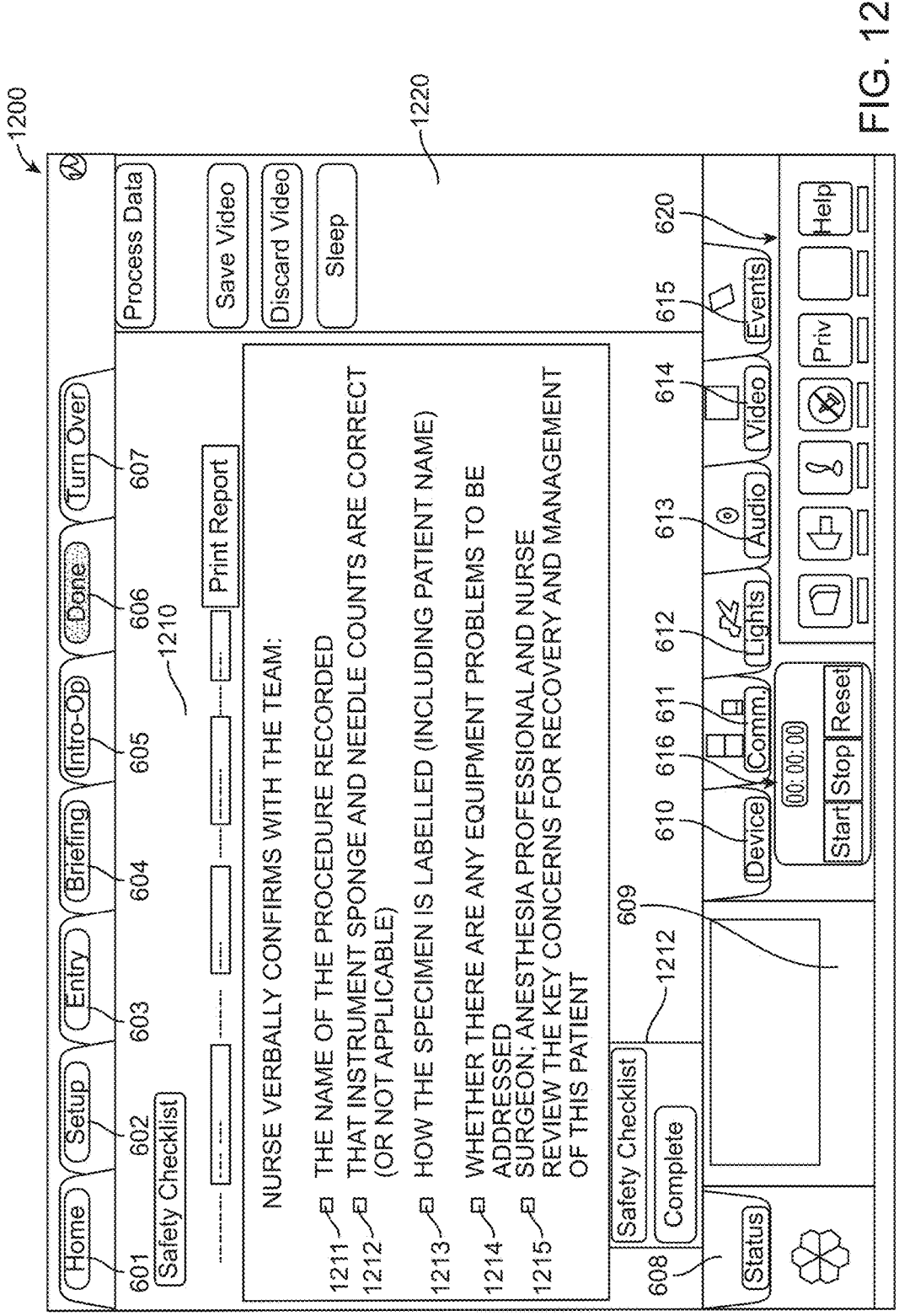
FIG. 12 a diagram of is an exemplary GUI display showing a done screen of the runtime application for the medical operation, according to the illustrative embodiment.
Figure 13:
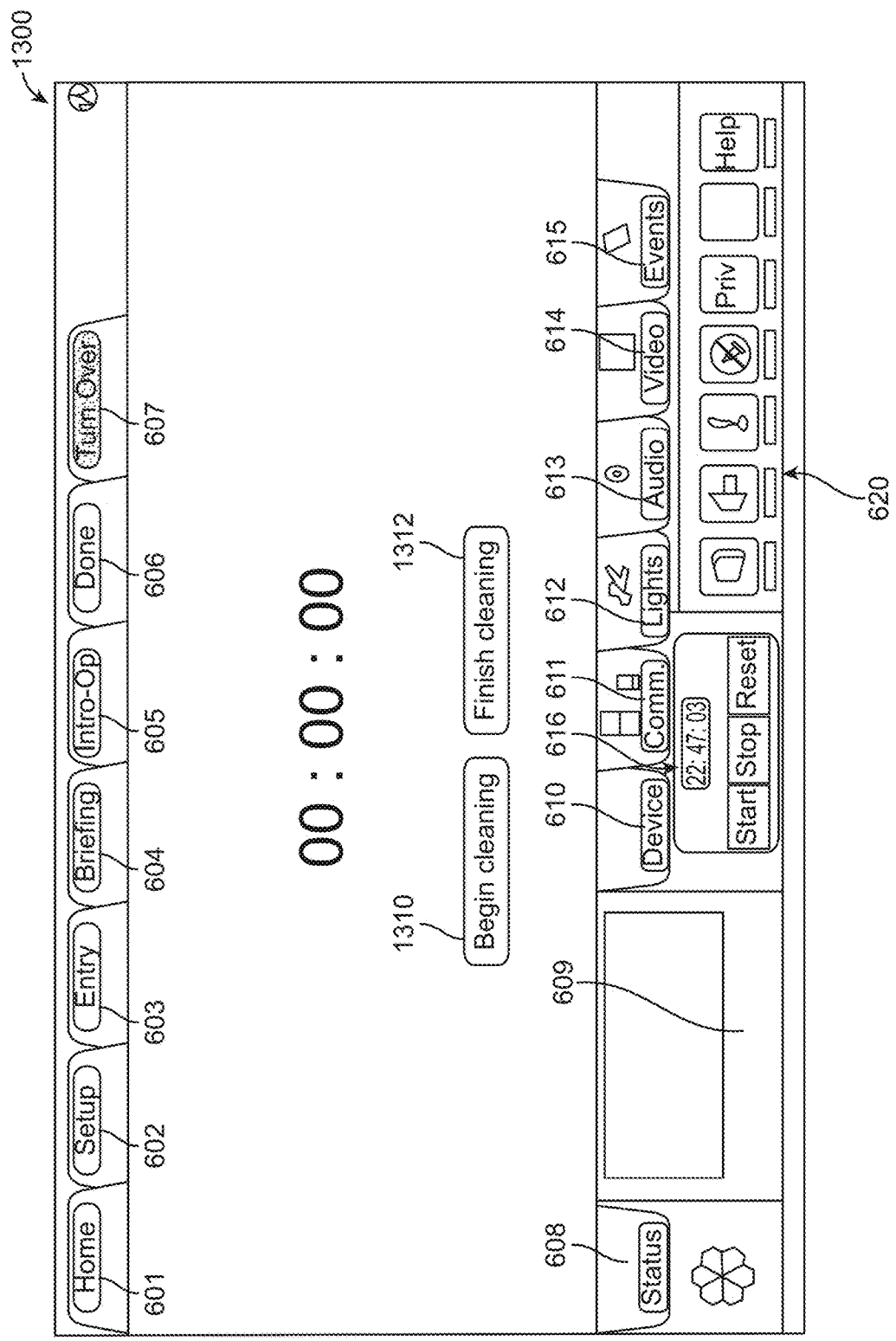
FIG. 13 a diagram of is an exemplary GUI display showing a turn over screen of the runtime application for the medical operation, according to the illustrative embodiment.
Figure 14:
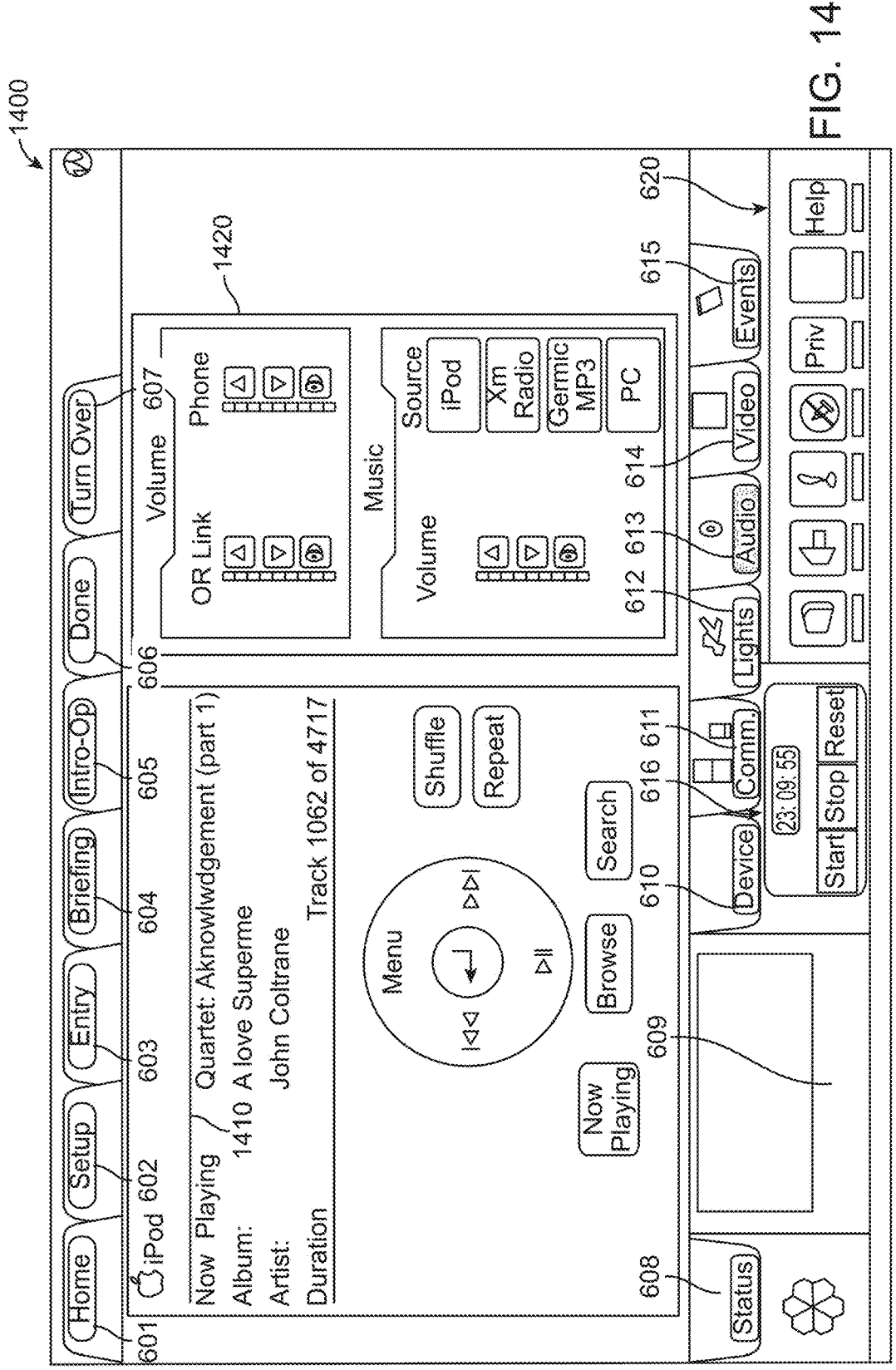
FIG. 14 a diagram of is an exemplary GUI display showing an audio settings screen of the runtime application for the medical operation, according to the illustrative embodiment.
Figure 15:
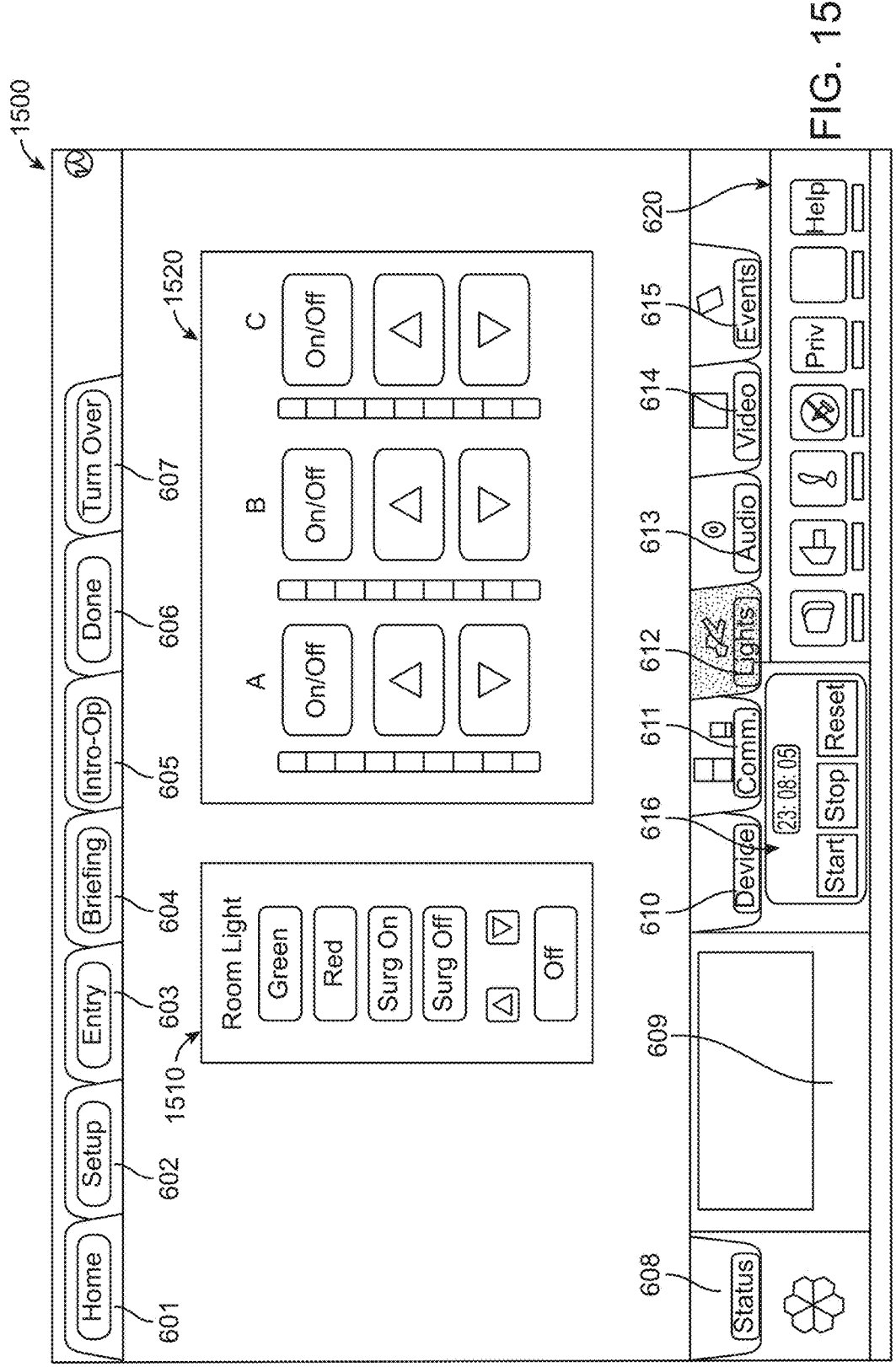
FIG. 15 a diagram of is an exemplary GUI display showing a lights settings screen of the runtime application for the medical operation, according to the illustrative embodiment.
Figure 16:
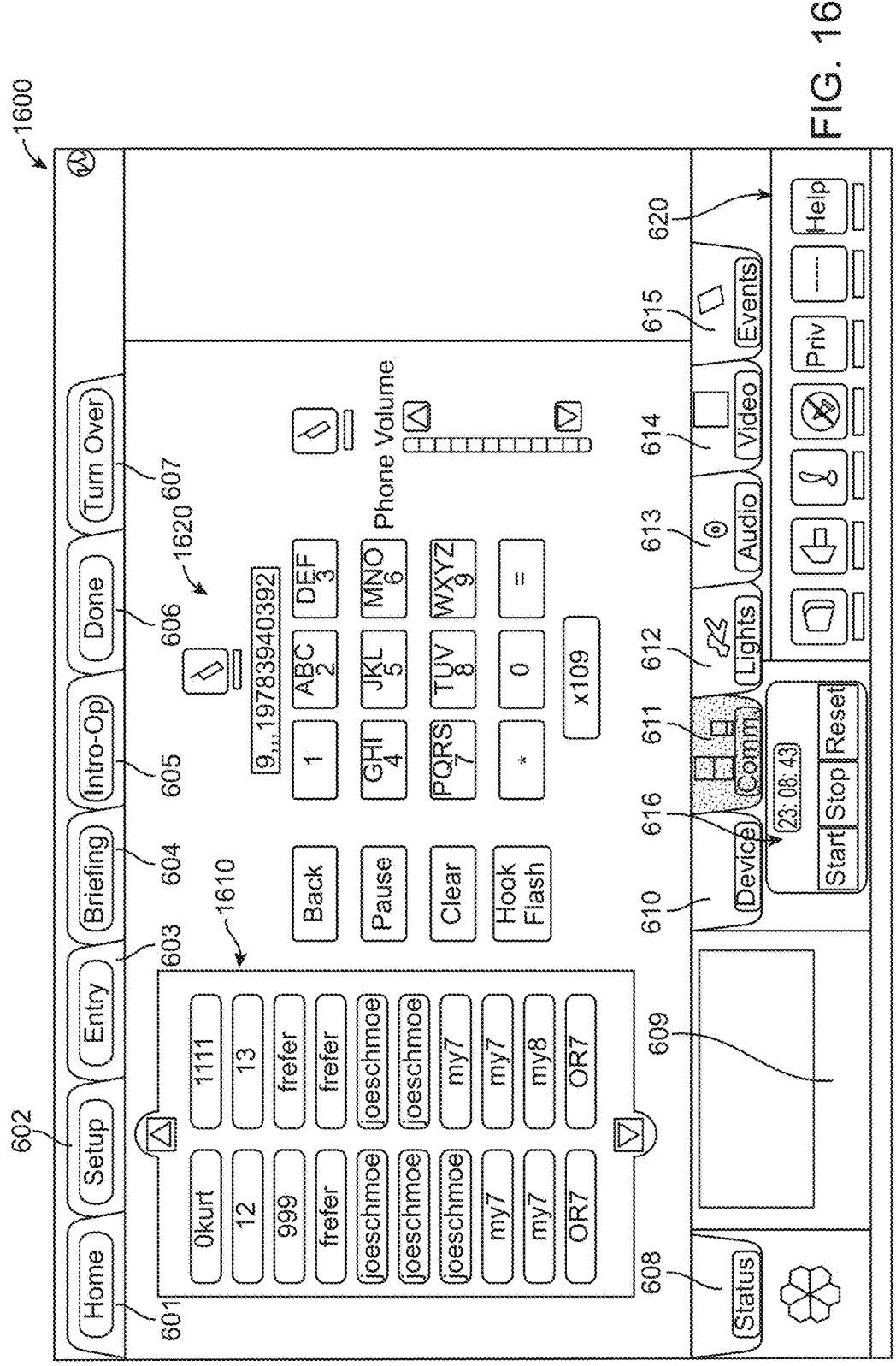
FIG. 16 a diagram of is an exemplary GUI display showing a communications screen of the runtime application for the medical operation, according to the illustrative embodiment.

At the end of the medical operation, the local user enters the done stage and is directed to a done screen 1200, as shown in the diagram of the exemplary GUI display of FIG. 12. The local user, a nurse or other person in the room, performs the safety checklist 1210 by performing the various required steps. Nurse verbally confirms point 1211 the name of the procedure, point 1212 the correct instrument, point 1213 the labeling of the specimen, point 1214 the equipment problems and point 1215 review key concerns. Data can then be processed by selecting an item from the process data panel 1220, including to save a video, discard a video, or send the system into a sleep mode. Once the safety checklist 1210 is complete, the local user completes the safety checklist by selecting the Complete button 1212. After the checklist is complete, the local user is directed to a turn over screen 1300 of the procedure, as shown in the exemplary GUI display of FIG. 13. The turn over screen 1300 includes a timer for room cleaning, with a begin cleaning button 1310 and a finish cleaning button 1312.

The exemplary GUI display also includes a plurality of tabs for adjusting the various settings within a particular room or performing various functions including the audio, video, lights, and communication in the room, among other settings and preferences. Selecting the "Audio" tab 613 directs the local user to an audio settings screen 1400, as shown in the exemplary GUI display of FIG. 14. The screen 1400 includes a virtual iPod 1410 which allows a user to select the audio to be played during the procedure, a volume panel 1420 to appropriately adjust volume and a music panel to adjust the volume of the various sources in relation to each other. The "Lights" tab 612 directs the local user to a lights settings screen 1500, as shown in the exemplary GUI display of FIG. 15. The screen 1500 includes a room light panel 1510 to select the light in the room. The amount of light is controlled using control panel 1520 to select the level of illumination and turn a light on or off as desired. Selecting the "Communication" tab 611 directs the local user to a communications screen 1600 which includes a speed-dial directory 1610 with a plurality of speed dial numbers saved therein for accessing a person. The speed-dial directory is managed by the VaultStream server, allowing information to be shared equally among all connected rooms. There is also provided a phone dial pad 1620 for dialing a phone number and performing other control of the phone.

Figure 17:
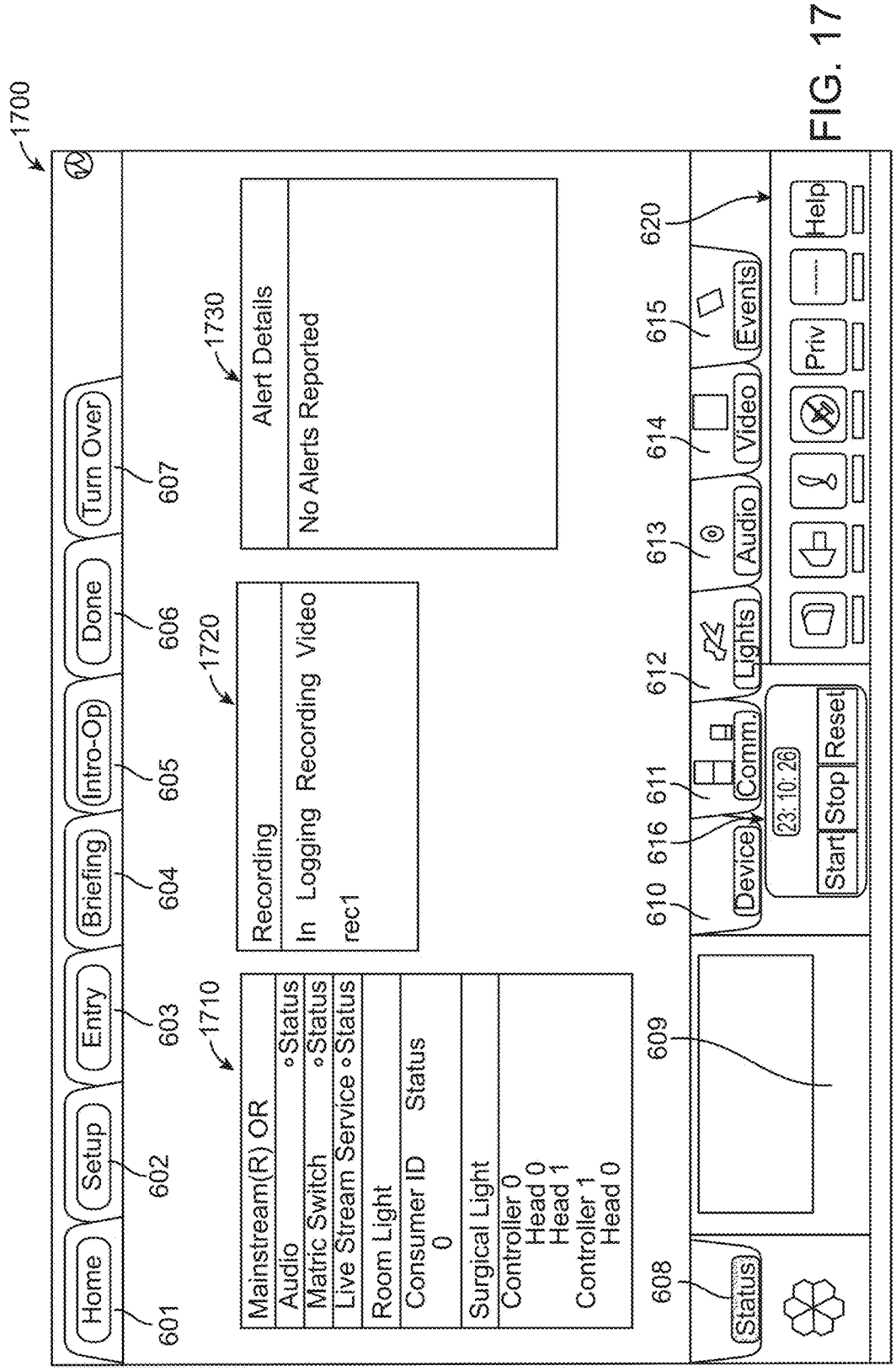
FIG. 17 a diagram of is an exemplary GUI display showing a safety board screen, according to the illustrative embodiment.

Selecting the "Status" tab 608 directs a support person to a status screen 1700, as shown in the exemplary GUI display of FIG. 17. The MainStream OR (operating room) panel 1710 shows the status of the devices and sources within the particular room. The Recording panel 1720 displays the status of any recording being performed. Any alert details are listed in the box 1730.

Figure 18:
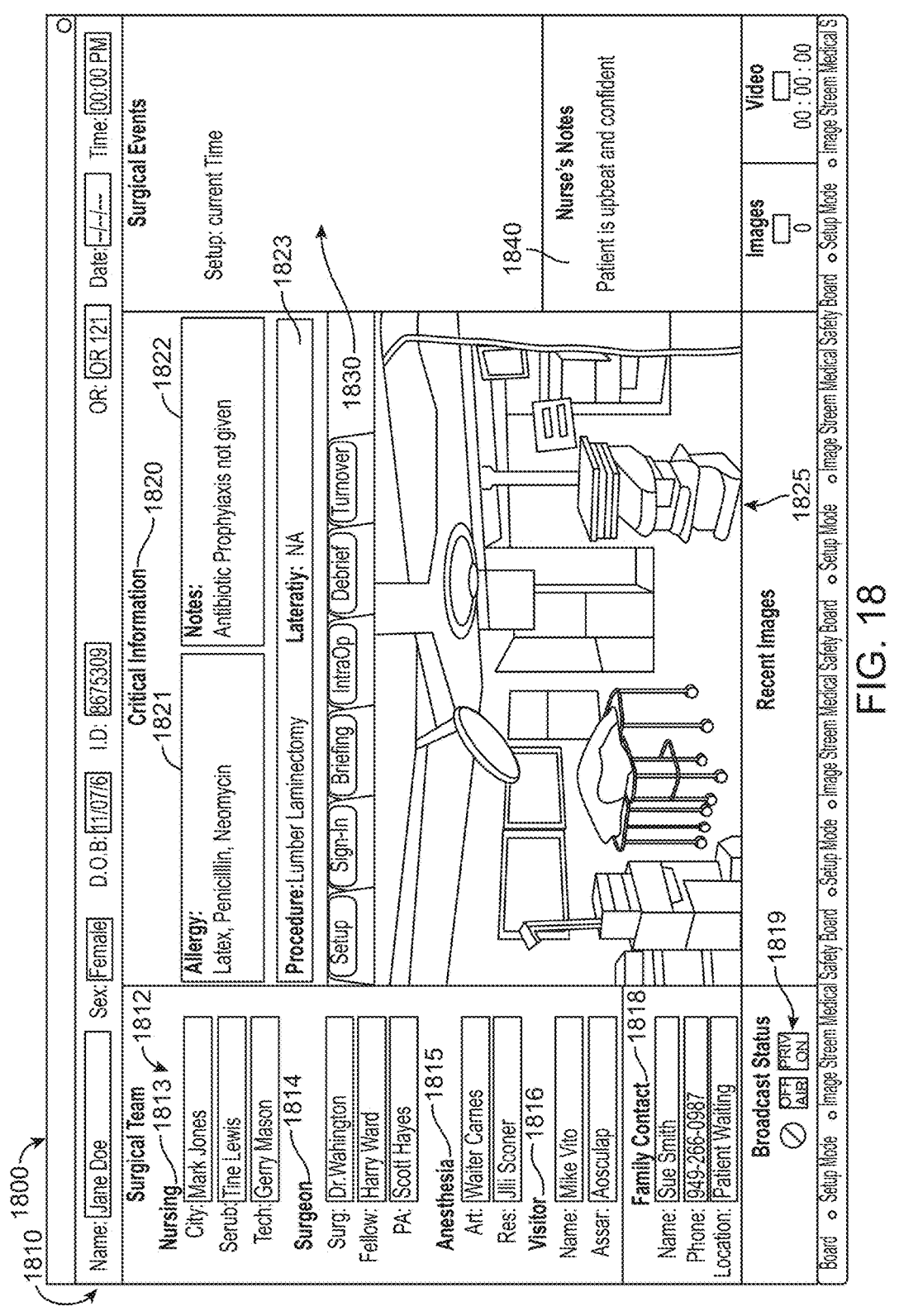

Reference is now made to FIG. 18, an exemplary GUI display showing a SafetyBoard setup screen 1800. The SafetyBoard provides demographics 1810 for a particular patient, information regarding the surgical team 1812, critical information 1820 for a patient, an event log 1830 and nurse's notes 1840. The SafetyBoard improves staff awareness and delivers key procedural information. It allows staff and personnel to gather pertinent information and view critical information for a patient. The Surgical team panel 1812 provides information regarding the nurses 1813, surgeon 1814, anesthesia 1815 and visitor 1816. The family contact information 1818 is also provided. The Broadcast status 1819 is also shown which indicates the status of streaming data. Critical information 1820 can include allergies 1821, notes 1822, procedure details 1823 and images 1825. The screen 1800 can also include surgery events 1830 and nurse's notes 1840. The majority of the information presented on the SafetyBoard can be acquired from the electronic hospital record system via HL7 communications over the hospital network.

Figure 19:
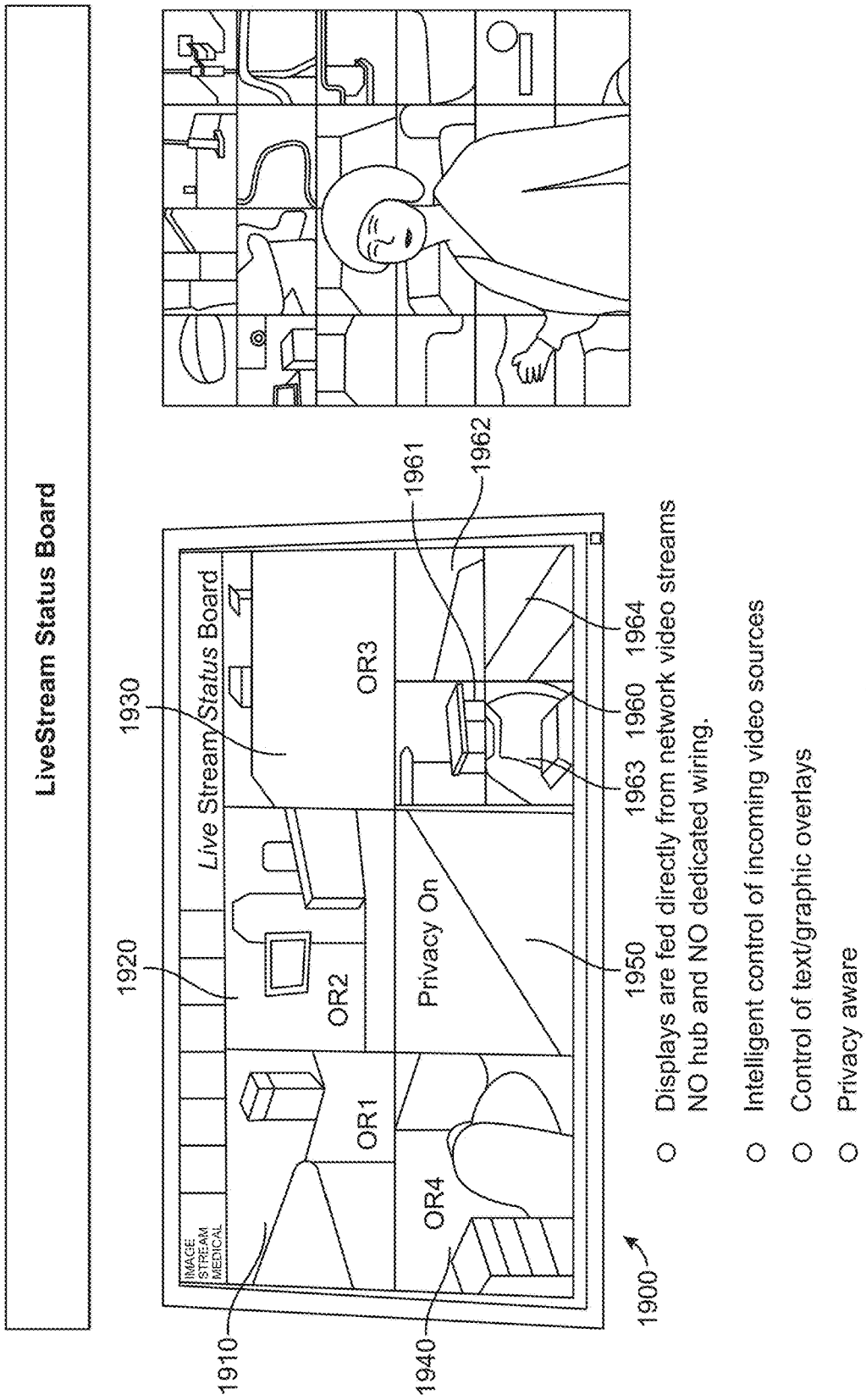
FIG. 19 a diagram of is an exemplary GUI display showing a status board screen, according to the illustrative embodiment.

FIG. 19 is an exemplary GUI display showing a Status Board screen 1900. The status board is a feature of the LiveStream system that allows the displays that are provided by MainStream to be fed directly to the display of the Status Board screen 1900 over the IP network. As shown, a plurality of individual windows 1910, 1920, 1930, 1940, 1950, 1960 (1961, 1962, 1963, 1964) are provided on a single board to view a plurality of sources. These are viewed directly through the network switch which transmits the data. Accordingly, there is no need for a video hub and no need for dedicated wiring for the system. Note that the screen 1950 has the privacy mode on so that the sources cannot be displayed. This indicates that a local user in a room has turned on the privacy mode so that the displays are not available for other viewers.

Figure 20:
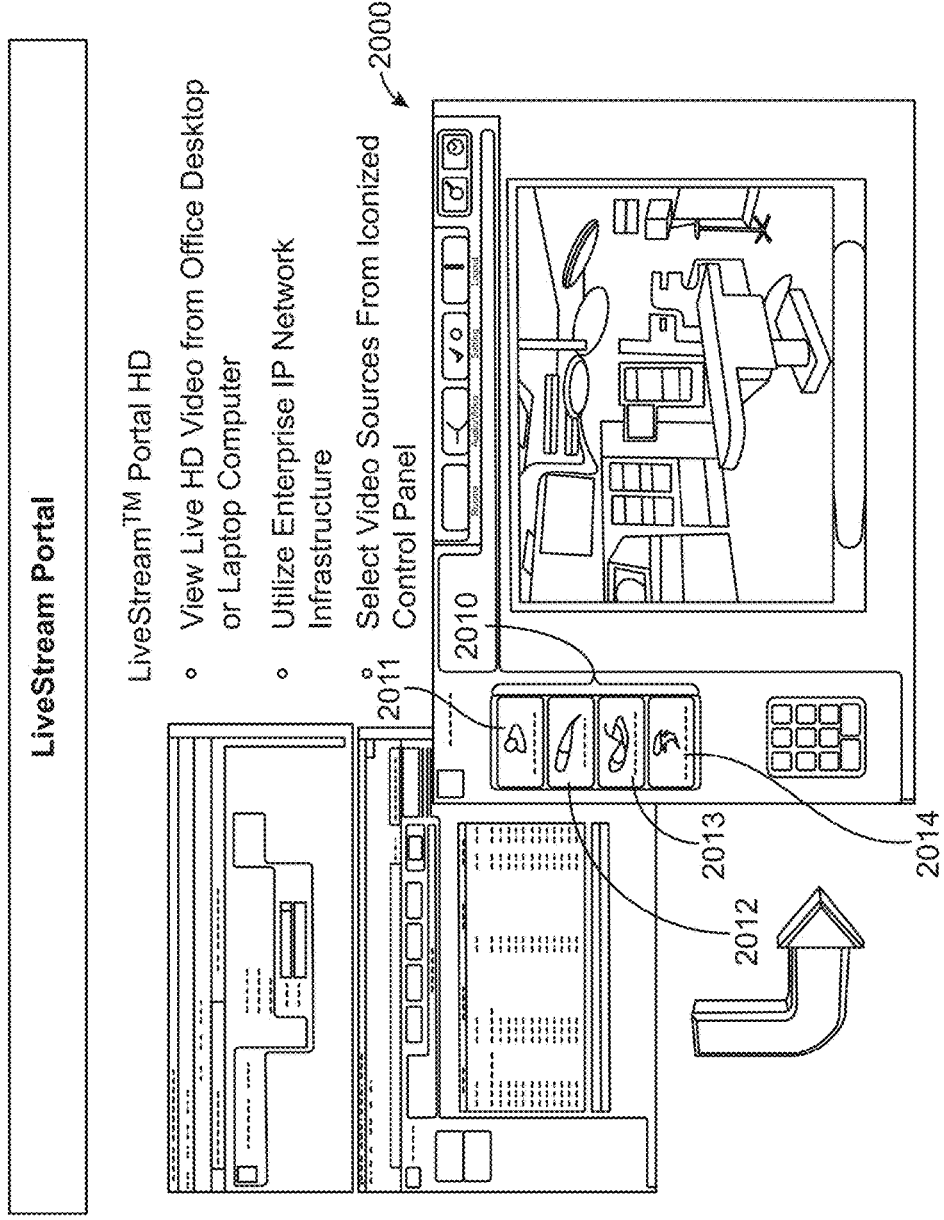
FIG. 20 a diagram of is an exemplary GUI display showing a portal screen, according to the illustrative embodiment.

FIG. 20 is an exemplary GUI display showing a web Portal screen 2000, the Portal being a feature of the LiveStream system that allows a remote viewer to view live video and select video sources from the control panel. As shown, a control panel 2010 is provided with icons each representing the various sources within the room. There is a room camera 2011, endoscope 2012, bronchoscope 2013 and standard microscope 2014. Each of these sources can be selected to view the source as it is viewed within the room, thereby creating a virtual presence for the remote viewer in the room. In addition, content can be provided and selected by the user in the form of display icons to further achieve the virtual presence effect.

The exemplary GUI displays described above employ the systems and methods described herein to implement the MainStream system and LiveStream server in the illustrative embodiments. The system provides an application for performing a medical procedure and allows the local user to have exclusive control of the procedure and functions associated with various sources. A remote viewer is able to view the available displays corresponding to the sources being controlled by the local user to create a virtual presence as though the remote viewer is in the room where the operation is being performed. The system improves communication by standardizing the format for switching and streaming files and content over a network.

Figure 21:
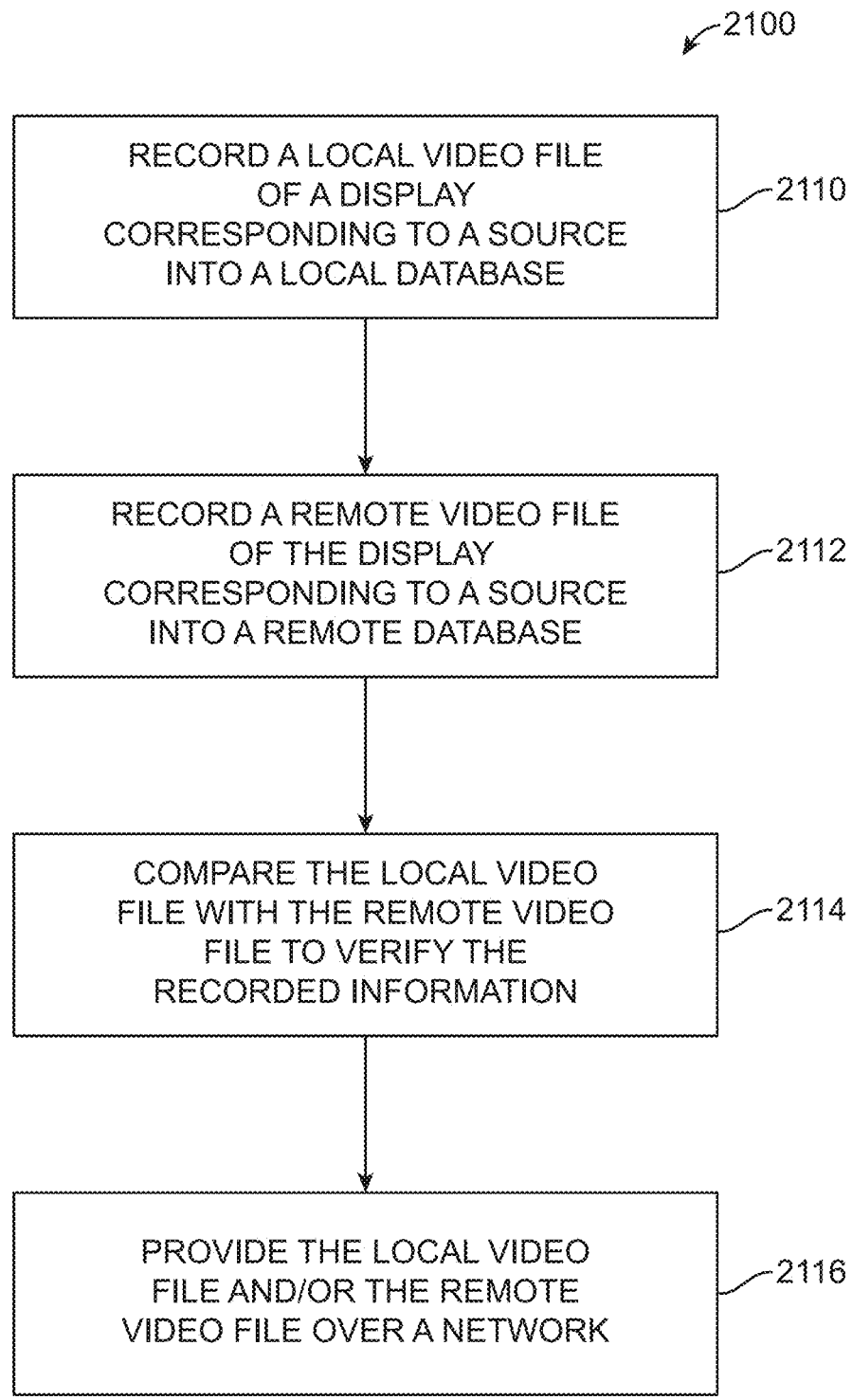
FIG. 21 is a flow chart showing a procedure for performing dual recording, according to the illustrative embodiment.

The teachings herein enable a VaultStream server (e.g. server 150 of FIG. 1) to control the recording of video files and other content such that a recording is stored in both a local database and a remote database. FIG. 21 is a flow chart showing a procedure 2100 for performing dual recording. At procedure step 2110 a local video file of a display corresponding to a source being used in the operation is recorded into a local database. At procedure step 2112 a remote video file of a display corresponding to a source is recorded in a remote database. Note that steps 2110 and 2112 can occur simultaneously so that the video file is recorded both locally and remotely at the same time, to provide the video files at both locations. The local video file and the remote video file are then compared at procedure step 2114 to verify the recorded information. This is accomplished by performing a comparison of the number of files present at each location, or a comparison of both content and duration of each video filing according to conventional comparative techniques. The local video file and/or remote video file can further be provided over a network at step 2116. In this manner, users can access both the local video file and the remote video file. Further, the transfer time is significantly decreased, as there is no need to transfer the files after the recording has occurred or started. Advantageously, this procedure ensures that the video files are available for remote viewers while they are simultaneously being recorded in a local database. The dual-recording system also enables workflow because the files are immediately accessible both locally and remotely.

Figure 22:
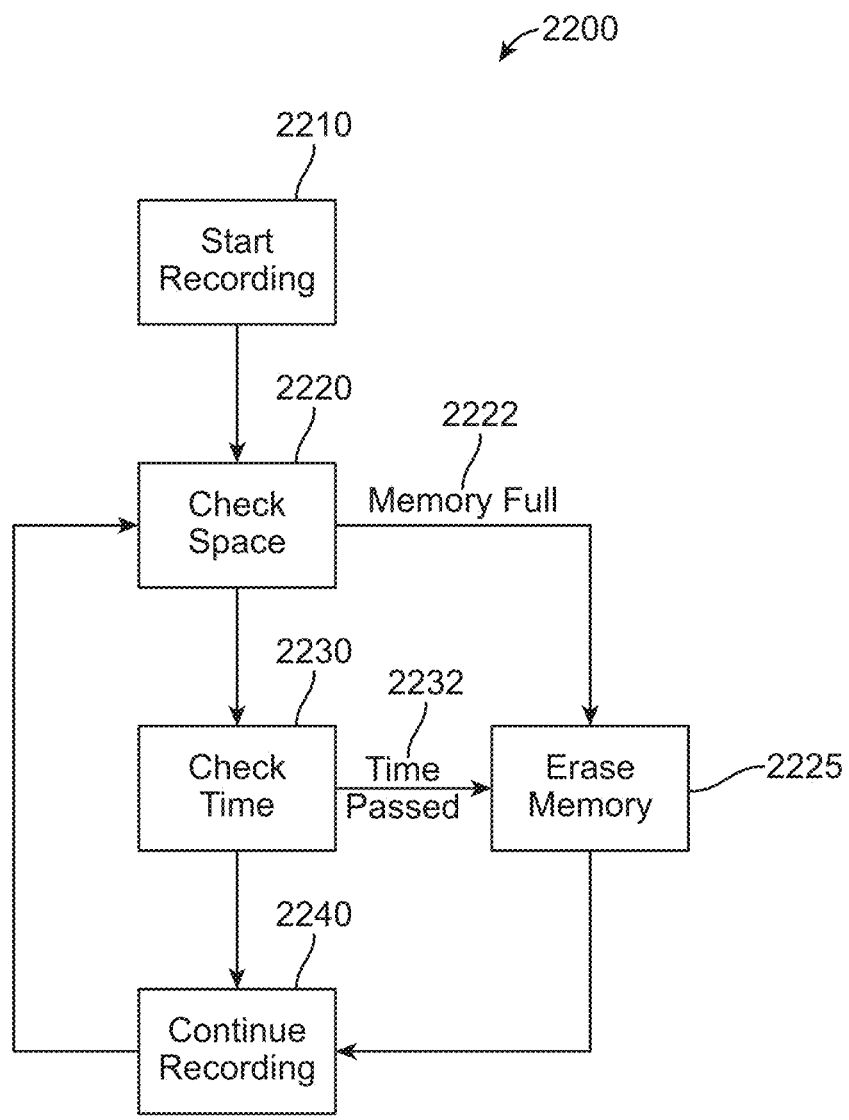
FIG. 22 is a flow chart of a procedure for implementing a continuous-loop recording system in accordance with the illustrative embodiments.

Reference is now made to FIG. 22 showing a flow chart of a procedure for continuous-loop recording in a medical environment. As shown, the procedure 2200 commences at step 2210 by starting the recording and then continues to record. In an illustrative embodiment, the system includes a database and application that stores data from cameras (the virtual presence cameras, for example, or other cameras or devices within the room) onto the database during the continuous record step. The continuous-loop recording system stores the data for a predetermined amount of time (for example, 1 day or 12 hours) or until the memory is full. However, if there is a problem, then the procedure stops and the data is available if something goes wrong in the room of the medical procedure. If there are no problems with a particular procedure continues to record in a loop, recording over previously recorded (and/or deleted) data such that a lesser amount of memory is employed to record.

With continued reference to FIG. 22, the procedure can be constructed and arranged to continue to check space in memory at 2220 and, if it is full at 2222, the procedure advances to erase memory at 2225. If the memory is not full at step 2220, the procedure continues to record and then checks if the predetermined amount of time has passed at step 2230. When the predetermined amount of time has passed at step 2230, the procedure advances to step 2225 to erase memory and then continue to record at step 2240. If not enough time has passed at 2230, the procedure continues recording at step 2240. In further embodiments, the erasing of memory at step 2225 can be optional, and the system can start the recording over the existing recorded data. In many medical environments, it is desirable to delete the existing memory after it is full or after the predetermined amount of time has passed, for security purposes and, where necessary, HIPAA compliance.

The devices, systems and methods shown and described herein improve usability of OR systems and streamline OR workflow, as well as usability and workflow of any medical environment in which a procedure is performed. The sources in the room are standardized for effective and efficient communication to allow for real-time access to live video streams.

The foregoing has been a detailed description of illustrative embodiments of the invention. Various modifications and additions can be made without departing from the spirit and scope of this invention. Each of the various embodiments described above may be combined with other described embodiments in order to provide multiple features. Moreover, while the foregoing describes a number of separate embodiments of the apparatus and method of the present invention, what has been described herein is merely illustrative of the application of the principles of the present invention. For example, specific arrangements of various components and entities of the system have been shown for illustrative purposes. However, any appropriate arrangement which employs the teachings herein is expressly contemplated. For example, the particular arrangement of various servers within a network is highly variable. Furthermore, appropriate access controls can be provided for the networked communication to comply with health insurance and data management standards, as appropriate. Additionally, several particular sources and medical procedures have been described for illustrative purposes, however any number of sources and medical procedures can implement the systems and methods described herein, without departing from the scope of this invention. Accordingly, this description is meant to be taken only by way of example, and not to otherwise limit the scope of this invention.

What is claimed is:

1. A computing device for creating a virtual presence for a remote viewer at a remote device, the computing device comprising:
    a memory;
    a first input configured to couple to a virtual presence camera located in a room of a medical facility in which a medical procedure is to be performed, wherein the computing device is configured to receive a first video stream of the room via the first input;
    a second input configured to couple to a source located in the room and associated with the medical procedure, wherein the computing device is configured to receive a second video stream from the source via the second input; and
    at least one processor coupled to the memory, the first input, and the second input and configured to:
        determine content available to the remote device, wherein the content includes one or more displays associated with the medical procedure or one or more sources associated with the medical procedure;
        include the second video stream in the content available to the remote device in response to a status indicating that the source is available during the medical procedure; and
        transmit the second video stream to the remote device.

2. The computing device of claim 1, wherein the at least one processor is further configured to determine, based on one or more statuses comprising the status, a list of one or more sources that are available to the remote device and the content comprises a 360-degree view of the room from the first video stream and the list.

3. The computing device of claim 1, wherein the status includes either a patient status, a room status, an equipment status, or a status indicative of a type of procedure to be performed in the room.

4. The computing device of claim 1, wherein the source comprises an endoscope.

5. The computing device of claim 1, wherein the computing device is in the room and the remote device is not in the room.

6. The computing device of claim 1, wherein the at least one processor is further configured to include the first video stream in the content.

7. The computing device of claim 1, wherein the at least one processor is further configured to receive the second video stream from the source via the second input and the content includes three different video streams each having a different resolution.

8. The computing device of claim 1, wherein the at least one processor is further configured to omit the first video stream and the second video stream from the content when the status indicates that the room is in a privacy mode.

9. The computing device of claim 1, wherein the at least one processor is further configured to:
receive a message transmitted over a network at the medical facility, the message including data;
analyze the data to determine the status; and
identify the source based on the status.

10. The computing device of claim 1, wherein the at least one processor is configured to automatically determine the status.

11. A method for creating, via a computing device, a virtual presence for a remote viewer at a remote device, the method comprising:
receiving, by a first input of the computing device, a first video stream from a virtual presence camera located in a room of a medical facility in which a medical procedure is to be performed;
receiving, by a second input of the computing device, a second video stream from a source in the room, the source being associated with the medical procedure;
determining, by at least one processor of the computing device, content available to the remote device, wherein the content includes one or more displays associated with the medical procedure or one or more sources associated with the medical procedure;
including, by the at least one processor of the computing device, the second video stream in the content available to the remote device in response to a status indicating that the source is available during the medical procedure; and
transmitting, by the at least one processor of the computing device, the second video stream to the remote device.

12. The method of claim 11, further comprising:
receiving, by the at least one processor, the second video stream from the source; and
including, in the content, three different video streams each having a different resolution.

13. The method of claim 11, further comprising analyzing data contained in a message transmitted over a network at the medical facility to determine the status.

14. The method of claim 11, further comprising automatically determining the status.

15. A system for creating a virtual presence for a remote viewer at a remote device, the system comprising:
a virtual presence camera in a room in a medical facility in which a medical procedure is to be performed, the virtual presence camera configured to generate a first video stream that provides a view of the room;
at least one source in the room, the at least one source being associated with the medical procedure and being configured to provide a second video stream; and
a computing device in the room, the computing device including a first input coupled to the virtual presence camera, a second input coupled to the at least one source, and at least one processor configured to:
determine content available to the remote device, wherein the content includes one or more displays associated with the medical procedure or one or more sources associated with the medical procedure,
include the second video stream in the content available to the remote device in response to a status indicating that the source is available during the medical procedure, and
transmit the second video stream to the remote device.

16. The system of claim 15, wherein the status includes either a patient status, a room status, an equipment status, or a status indicative of a type of procedure to be performed in the room.

17. The system of claim 15, wherein the source is an endoscope and the status indicates that the endoscope is available during the medical procedure.

18. The system of claim 15, wherein the at least one processor is further configured to receive the second video stream from the source via the second input and the content includes three different video streams each having a different resolution.

19. The system of claim 15, wherein the at least one processor is further configured to:
receive a message transmitted over a network at the medical facility, the message including data;
analyze the data to determine the status; and
identify the source based on the status.

20. The system of claim 15, wherein the at least one processor is configured to automatically determine the status.

* * * * *